US012576110B2

(12) United States Patent
Biffi et al.

(10) Patent No.: US 12,576,110 B2
(45) Date of Patent: Mar. 17, 2026

(54) METHODS AND COMPOSITIONS FOR RECONSTITUTING MICROGLIA

(71) Applicants: The Children's Medical Center Corporation, Boston, MA (US); Dana-Farber Cancer Institute, Inc., Boston, MA (US)

(72) Inventors: Alessandra Biffi, Boston, MA (US); Annita Montepeloso, Boston, MA (US)

(73) Assignees: The Children's Medical Center Corporation, Boston, MA (US); Dana-Farber Cancer Institute, Inc., Boston, MA (US)

( * ) Notice: Subject to any disclaimer, the term of this patent is extended or adjusted under 35 U.S.C. 154(b) by 989 days.

(21) Appl. No.: 17/632,752

(22) PCT Filed: Aug. 6, 2020

(86) PCT No.: PCT/US2020/045106
§ 371 (c)(1),
(2) Date: Feb. 3, 2022

(87) PCT Pub. No.: WO2021/026294
PCT Pub. Date: Feb. 11, 2021

(65) Prior Publication Data
US 2022/0323503 A1     Oct. 13, 2022

Related U.S. Application Data

(60) Provisional application No. 62/883,428, filed on Aug. 6, 2019.

(51) Int. Cl.
| | |
|---|---|
| *A61K 35/28* | (2015.01) |
| *A61K 31/255* | (2006.01) |
| *A61P 25/00* | (2006.01) |
| *C07K 14/715* | (2006.01) |

(52) U.S. Cl.
CPC ............ *A61K 35/28* (2013.01); *A61K 31/255* (2013.01); *A61P 25/00* (2018.01); *C07K 14/7158* (2013.01)

(58) Field of Classification Search
None
See application file for complete search history.

(56) References Cited

U.S. PATENT DOCUMENTS

| | | | |
|---|---|---|---|
| 8,697,359 | B1 | 4/2014 | Zhang |
| 2012/0192298 | A1 | 7/2012 | Weinstein et al. |
| 2014/0170753 | A1 | 6/2014 | Zhang |
| 2014/0179006 | A1 | 6/2014 | Zhang |
| 2014/0179770 | A1 | 6/2014 | Zhang et al. |
| 2014/0186843 | A1 | 7/2014 | Zhang et al. |
| 2014/0186958 | A1 | 7/2014 | Zhang et al. |
| 2014/0189896 | A1 | 7/2014 | Zhang et al. |
| 2014/0227787 | A1 | 8/2014 | Zhang |

| | | | |
|---|---|---|---|
| 2014/0242664 | A1 | 8/2014 | Zhang et al. |
| 2014/0248702 | A1 | 9/2014 | Zhang et al. |
| 2014/0256046 | A1 | 9/2014 | Zhang et al. |
| 2014/0273230 | A1 | 9/2014 | Chen et al. |
| 2014/0273233 | A1 | 9/2014 | Chen et al. |
| 2014/0273234 | A1 | 9/2014 | Zhang et al. |
| 2014/0295556 | A1 | 10/2014 | Joung et al. |
| 2014/0295557 | A1 | 10/2014 | Joung et al. |
| 2014/0310830 | A1 | 10/2014 | Zhang et al. |
| 2014/0356956 | A1 | 12/2014 | Church et al. |
| 2014/0356959 | A1 | 12/2014 | Church et al. |
| 2014/0357530 | A1 | 12/2014 | Zhang et al. |
| 2015/0020223 | A1 | 1/2015 | Zhang et al. |
| 2015/0031132 | A1 | 1/2015 | Church et al. |
| 2015/0031133 | A1 | 1/2015 | Church et al. |
| 2015/0031134 | A1 | 1/2015 | Zhang et al. |
| 2015/0044191 | A1 | 2/2015 | Liu et al. |
| 2015/0044192 | A1 | 2/2015 | Liu et al. |
| 2015/0045546 | A1 | 2/2015 | Siksnys et al. |
| 2015/0050699 | A1 | 2/2015 | Siksnys et al. |
| 2015/0056705 | A1 | 2/2015 | Conway et al. |

(Continued)

FOREIGN PATENT DOCUMENTS

| | | |
|---|---|---|
| WO | 2018035388 A1 | 2/2018 |
| WO | 2018071898 A1 | 4/2018 |
| WO | 2019051424 A2 | 3/2019 |

OTHER PUBLICATIONS

Ajami et al., "Infiltrating monocytes trigger EAE progression, but do not contribute to the resident microglia pool," Nature Neuroscience, Sep. 2011, vol. 14, No. 9, pp. 1142-1149.
Ajami et al., "Local self-renewal can sustain CNS microglia maintenance and function throughout adult life," Nature Neuroscience, Dec. 2007, vol. 10, No. 12, pp. 1538-1543.
Biffi et al., "Gene therapy of metachromatic leukodystrophy reverses neurological damage and deficits in mice," The Journal of Clinical Investigation, Nov. 2006, vol. 116, No. 11, pp. 3070-3082.
Biffi et al., "Lentiviral Hematopoietic Stem Cell Gene Therapy Benefits Metachromatic Leukodystrophy," Science, Aug. 23, 2013, vol. 341, pp. 1233158-1-1233158-11.

(Continued)

*Primary Examiner* — Blaine Lankford
(74) *Attorney, Agent, or Firm* — Greenberg Traurig, LLP; Melissa Hunter-Ensor; Nathan Hsu

(57) ABSTRACT

The present disclosure features CX3CR1 hemizygous and/or homozygous defective cells and methods of using such cells for the treatment of a metabolic or neurological disorder. The disclosed methods include methods for making and modifying CX3CR1 hemizygous and/or homozygous defective cells, such as hematopoietic stem progenitor cells. Other disclosed methods include methods of treating a subject having or suspected of having a metabolic or neurological disease comprising administering to the subject a composition comprising a hemizygous and/or homozygous defective CX3CR1 cell. The CX3CR1 hemizygous and/or homozygous defective cell may be modified to have a nucleic acid molecule encoding a therapeutic polypeptide or polynucleotide.

14 Claims, 16 Drawing Sheets
Specification includes a Sequence Listing.

(56)                    References Cited

U.S. PATENT DOCUMENTS

| | | |
|---|---|---|
| 2015/0071898 A1 | 3/2015 | Liu et al. |
| 2015/0071899 A1 | 3/2015 | Liu et al. |
| 2015/0071903 A1 | 3/2015 | Liu et al. |
| 2015/0079681 A1 | 3/2015 | Zhang |
| 2015/0159172 A1 | 6/2015 | Miller et al. |
| 2015/0165054 A1 | 6/2015 | Liu et al. |
| 2015/0166980 A1 | 6/2015 | Liu et al. |
| 2015/0184139 A1 | 7/2015 | Zhang et al. |
| 2016/0068844 A1 | 3/2016 | Wadsworth et al. |
| 2020/0038439 A1* | 2/2020 | Biffi .......................... A61K 9/51 |

OTHER PUBLICATIONS

Butovsky et al., "Identification of a Unique TGF-β Dependent Molecular and Functional Signature in Microglia," Nature Neuroscience, Jan. 2014, vol. 17, No. 1, pp. 131-143.

Capotondo et al., "Brain conditioning is instrumental for successful microglia reconstitution following hematopoietic stem cell transplantation," Proceedings of the National Academy of Sciences of the United States of America, Sep. 11, 2012, vol. 109, No. 37, pp. 15018-15023.

Cartier et al., "Hematopoietic Stem Cell Gene Therapy with a Lentiviral Vector in X-Linked Adrenoleukodystrophy," Science, Nov. 6, 2009, vol. 326, pp. 818-823.

Eichler et al., "Is Microglial Apoptosis an Early Pathogenic Change in Cerebral X-Linked Adrenoleukodystrophy?," Annals of Neurology, Jun. 2008, vol. 63, No. 6, pp. 729-742.

Ginhoux et al., "Fate Mapping Analysis Reveals That Adult Microglia Derive from Primitive Macrophages," Science, Nov. 5, 2010, vol. 330, pp. 841-845.

Jeyakumar et al., "Central nervous system inflammation is a hallmark of pathogenesis in mouse models of GM1 and GM2 gangliosidosis," Brain, 2003, vol. 126, pp. 974-987.

Mildner et al., "Microglia in the adult brain arise from Ly-6ChiCCR2+ monocytes only under defined host conditions," Nature Neuroscience, Dec. 2007, vol. 10, No. 12, pp. 1544-1553.

Ohmi et al., "Activated microglia in cortex of mouse models of mucopolysaccharidoses I and IIIB," Proceedings of the National Academy of Sciences of the United States of America, Feb. 18, 2003, vol. 100, No. 4, pp. 1902-1907.

Sessa et al., "Lentiviral haemopoietic stem-cell gene therapy in early-onset metachromatic leukodystrophy: an ad-hoc analysis of a non-randomised, open-label, phase 1/2 trial," The Lancet, Jul. 30, 2016, vol. 388, pp. 476-487.

Simard et al., "Bone Marrow-Derived Microglia Play a Critical Role in Restricting Senile Plaque Formation in Alzheimer's Disease," Neuron, Feb. 16, 2006, vol. 49, pp. 489-502.

Verdonk et al., "Phenotypic clustering: a novel method for microglial morphology analysis," Journal of Neuroinflammation, 2016, vol. 13, Article No. 153, pp. 1-15.

Wada et al., "Microglial activation precedes acute neurodegeneration in Sandhoff disease and is suppressed by bone marrow transplantation," Proceedings of the National Academy of Sciences of the United States of America, Sep. 26, 2000, vol. 97, No. 20, pp. 10954-10959.

Wilkinson et al., "Busulfan Conditioning Enhances Engraftment of Hematopoietic Donor-derived Cells in the Brain Compared With Irradiation," Molecular Therapy, Apr. 2013, vol. 21, No. 4, pp. 868-876.

Chen et al., "The neuroprotective roles of BDNF in hypoxic ischemic brain injury (Review)," Biomedical Reports, 2013, vol. 1, No. 2, pp. 167-176; Published Online Dec. 14, 2012.

International Search Report and Written Opinion mailed Nov. 23, 2020 in corresponding PCT Patent Application No. PCT/US2020/045106 (10 pages).

Asheuer et al., "Human CD34+ cells differentiate into microglia and express recombinant therapeutic protein," Proceedings of the National Academy of Sciences of the United States of America, Mar. 9, 2004, vol. 101, No. 10, pp. 3557-3562.

Capotondo et al., "Intracerebroventricular delivery of hematopoietic progenitors results in rapid and robust engraftment of microglia-like cells," Science Advances, Dec. 2017, vol. 3, e1701211, pp. 1-12.

Cook et al., "Generation and Analysis of Mice Lacking the Chemokine Fractalkine," Molecular and Cellular Biology, May 2001, vol. 21, No. 9, pp. 3159-3165.

Fuhrmann et al., "Microglial Cx3cr1 knockout prevents neuron loss in a mouse model of Alzheimer's disease," Nature Neuroscience, Apr. 2010, vol. 13, No. 4, pp. 411-413.

Jung et al., "Analysis of Fractalkine Receptor CX3CR1 Function by Targeted Deletion and Green Fluorescent Protein Reporter Gene Insertion," Molecular and Cellular Biology, Jun. 2000, vol. 20, No. 11, pp. 4106-4114.

Lee et al., "CX3CR1 Deficiency Alters Microglial Activation and Reduces Beta-Amyloid Deposition in Two Alzheimer's Disease Mouse Models," The American Journal of Pathology, Nov. 2010, vol. 177, No. 5, pp. 2549-2562.

Lewis, Coral-Ann B., "Investigations Into The Accumulation of Hematopoietic Cells In The Spinal Cord In A Murine Model of Motor Neuron Disease," Thesis, Simon Fraser University, Summer 2011, pp. 1-212.

Extended European Search Report dated Jul. 10, 2023 in corresponding European Patent Application No. 20849655.4 (10 pages).

* cited by examiner

Donor CD45.2

Hematopoietic Organs Engraftment

Hematopoietic Organs donor cell composition

Sholl analysis

IV Tpx

ICV Tpx

Engraftment

Brain Engraftment

Hematopoietic Organs & Brain donor cell composition

BM lineages cell composition

Spleen lineages cell composition

METHODS AND COMPOSITIONS FOR RECONSTITUTING MICROGLIA

CROSS REFERENCE TO RELATED APPLICATIONS

This application is the U.S. National Stage Application, pursuant to 35 U.S.C. § 371 of PCT International Application No. PCT/US2020/045106, filed Aug. 6, 2020 designating the United States and published in English, which claims priority to and the benefit of U.S. App. No. 62/883,428 filed Aug. 6, 2019, the entire contents of each of which are hereby incorporated by reference in its their entirety.

SEQUENCE LISTING

The instant application contains a Sequence Listing which has been submitted electronically in ASCII format and is hereby incorporated by reference in its entirety. Said ASCII copy, created on Sep. 9, 2020, is named 167705_017101 PCT SL.txt and is 5,461 bytes in size.

BACKGROUND OF THE INVENTION

Recent findings indicate that hematopoietic stem and progenitor cells (HSPCs) can contribute to the turnover of resident brain myeloid cell populations upon administration of a conditioning regimen. In the context of metabolic and neurological diseases, engrafted cells can act as vehicles to deliver neuroprotective agents to the brains of affected patients. However, this approach has not been extensively adopted for the treatment of neurological and metabolic diseases due to the slow engraftment and expansion of the transplanted HSPCs and their progeny, as compared with the rapid progression of the neurological disease. Thus, there is a need for improved methods of HSPC transplantation. This disclosure is directed to this and other important needs.

SUMMARY OF THE INVENTION

As described below, the present disclosure features methods and compositions directed to enhancing engraftment of transplanted hematopoietic stem progenitor cells and their progeny in a subject in need thereof.

In one aspect, the invention provides a CX3CR1 hemizygous or homozygous defective cell that includes an exogenous nucleic acid molecule encoding a therapeutic polynucleotide or polypeptide. In an embodiment, the exogenous nucleic acid molecule is inserted into the cell's genome at the CX3CR1 gene locus. In an embodiment, the therapeutic polynucleotide or polypeptide is neuroprotective.

In another aspect, the invention provides a pharmaceutical composition which includes any of the above CX3CR1 hemizygous and/or homozygous defective cells.

In another aspect, the invention provides a kit that includes any of the above described CX3CR1 hemizygous and/or homozygous defective cells and directions for the administration of the cell to a subject in need thereof.

In another aspect, the invention provides a kit that includes the pharmaceutical composition described above.

In another aspect, the invention provides a method of reconstituting microglia cells in a subject involving administering to the subject any of the above described CX3CR1 hemizygous and/or homozygous defective cells.

In another aspect, the invention provides a method of reconstituting microglia cells in a subject in which the method involves administering to the subject the pharmaceutical composition described above.

In another aspect, the invention provides a method of treating a metabolic or neurological disease in a subject, the method involving administering to the subject the above-described CX3CR1 hemizygous and/or homozygous defective cells. In various embodiments of the methods above, the administering is intracerebroventricular. In various embodiments of the methods above, the administering is intravenous. In various embodiments of the methods above, the methods further involve ablative conditioning prior to administering the pharmaceutical composition. In an embodiment, the ablative conditioning involves administering an alkylating agent capable of ablating endogenous microglia cells. In an embodiment, the alkylating agent is busulfan.

Compositions and methods defined in this disclosure were isolated or otherwise manufactured in connection with the examples provided below. Other features and advantages of the invention will be apparent from the detailed description, and from the claims.

Definitions

Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them below, unless specified otherwise.

As used herein, "ablative conditioning" refers to administering to a subject a composition that destroys endogenous hematopoietic stem and progenitor cells in the bone marrow niche, and functionally defined microglia progenitors in the central nervous system.

By "agent" is meant any small molecule chemical compound, antibody, nucleic acid molecule, or polypeptide, or fragments thereof.

By "alteration" is meant a change (increase or decrease) in the expression levels or activity of a gene or polypeptide as detected by standard art known methods such as those described herein. As used herein, an alteration includes a 10% change in expression levels, a 25% change, a 40% change, and a 50% or greater change in expression levels.

By "ameliorate" is meant decrease, suppress, attenuate, diminish, arrest, or stabilize the development or progression of a disease.

By "biologic sample" is meant any tissue, cell, fluid, or other material derived from an organism.

In this disclosure, "comprises," "comprising," "containing," and "having" and the like can have the meaning ascribed to them in U.S. Patent law and can mean "includes," "including," and the like; "consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

By "CX3CR1 protein" or "human beta chemokine recep-
tor-like 1 protein" is meant a protein having at least about
85% amino acid sequence identity to GenBank Accession
No.: ABS29268.1 or a fragment thereof and is a receptor for
fractalkine. An exemplary CX3CR1 polypeptide sequence is
provided below.
>AAA87032.1 beta chemokine receptor-like 1 [*Homo sapi-
ens*]

MDQFPESVTENFEYDDLAEACYIGDIVVFGTVFLSIFYSVIFAIGLVGNL

LVVFALTNSKKPKSVTDIYLLNLALSDLLFVATLPFWTHYLINEKGLHNA

MCKFTTAFFFIGFFGSIFFITVISIDRYLAIVLAANSMNNRTVQHGVTIS

LGVWAAAILVAAPQFMFTKQKENECLGDYPEVLQEIWPVLRNVETNFLGF

LLPLLIMSYCYFRIIQTLFSCKNHKKAKAIKLILLVVIVFFLFWTPYNVM

IFLETLKLYDFFPSCDMRKDLRLALSVTETVAFSHCCLNPLIYAFAGEKF

RRYLYHLYGKCLAVLCGRSVHVDFSSSESQRSRHGSVLSSNFTYHTSDGD

ALLLL

By "CX3CR1 polynucleotide" or "human beta chemokine
receptor-like polynucleotide" is meant a nucleic acid mol-
ecule encoding an CX3CR1 polypeptide. The CX3CR1 gene
encodes a receptor for fractalkine. An exemplary CX3CR1
polynucleotide sequence is provided below:
>U28934.1 Human beta chemokine receptor-like 1 mRNA,
complete cds

GGGGCAGATCCAGATTCCCTTTGCAGTCCACGCCAGGCCTTCACCATGGA

TCAGTTCCCTGAATCAGTGACAGAAAACTTTGAGTACGATGATTTGGCTG

AGGCCTGTTATATTGGGGACATCGTGGTCTTTGGGACTGTGTTCCTGTCC

ATATTCTACTCCGTCATCTTTGCCATTGGCCTGGTGGGAAATTTGTTGGT

AGTGTTTGCCCTCACCAACAGCAAGAAGCCCAAGAGTGTCACCGACATTT

ACCTCCTGAACCTGGCCTTGTCTGATCTGCTGTTTGTAGCCACTTTGCCC

TTCTGGACTCACTATTTGATAAATGAAAAGGGCCTCCACAATGCCATGTG

CAAATTCACTACCGCCTTCTTCTTCATCGGCTTTTTTGGAAGCATATTCT

TCATCACCGTCATCAGCATTGATAGGTACCTGGCCATCGTCCTGGCCGCC

AACTCCATGAACAACCGGACCGTGCAGCATGGCGTCACCATCAGCCTAGG

CGTCTGGGCAGCAGCCATTTTGGTGGCAGCACCCCAGTTCATGTTCACAA

AGCAGAAAGAAAATGAATGCCTTGGTGACTACCCCGAGGTCCTTCAGGAA

ATCTGGCCCGTGCTCCGCAATGTGGAAACAAATTTTCTTGGCTTCCTACT

CCCCCTGCTCATTATGAGTTATTGCTACTTCAGAATCATCCAGACGCTGT

TTTCCTGCAAGAACCACAAGAAAGCCAAAGCCATTAAACTGATCCTTCTG

GTGGTCATCGTGTTTTTCCTCTTCTGGACACCCTACAACGTTATGATTTT

CCTGGAGACGCTTAAGCTCTATGACTTCTTTCCCAGTTGTGACATGAGGA

AGGATCTGAGGCTGGCCCTCAGTGTGACTGAGACGGTTGCATTTAGCCAT

TGTTGCCTGAATCCTCTCATCTATGCATTTGCTGGGGAGAAGTTCAGAAG

ATACCTTTACCACCTGTATGGGAAATGCCTGGCTGTCCTGTGTGGGCGCT

CAGTCCACGTTGATTTCTCCTCATCTGAATCACAAAGGAGCAGGCATGGA

AGTGTTCTGAGCAGCAATTTTACTTACCACACGAGTGATGGAGATGCATT

GCTCCTTCTCTGAAGGGAATCCCAAAGCCTTGTGTGTCTACAGAGAACCTGG

AGTTCCTGAACCTGATGCTGACTAGTGAGGAAGATTTTTGTTGTTATTTC

TTACAGGCACAAAATGATGGACCCAATGCACACAAAACAACCCTAGAGTG

TTGTTGAGAATTGTGCTCAAAATTTGAAGAATGAACAAATTGAACTCTTT

GAATGACAAAGAGTAGACATTTCTCTTACTGCAAATGTCATCAGAACTTT

TTGGTTTGCAGATGACAAAAATTCAACTCAGACTAGTTTAGTTAAATGAG

GGTGGTGAATATTGTTCATATTGTGGCACAAGCAAAAAGGGTGTCTGAGC

CCTCAAAGTGAGGGGAACCAGGGCCTGAGCCAAGCTA

The term "hemizygous" as applied to CX3CR1 refers to
an otherwise diploid cell having only one copy of the
CX3CR1 gene.

As used herein, the terms "determining," "assessing,"
"assaying," "measuring," and "detecting" refer to both quan-
titative and qualitative determinations, and as such, the term
"determining" is used interchangeably herein with "assay-
ing," "measuring," and the like. Where a quantitative deter-
mination is intended, the phrase "determining an amount" of
an analyte and the like is used. Where a qualitative and/or
quantitative determination is intended, the phrase "deter-
mining a level" of an analyte or "detecting" an analyte is
used.

"Detect" refers to identifying the presence, absence or
amount of the analyte to be detected.

By "detectable label" is meant a composition that when
linked to a molecule of interest renders the latter detectable,
via spectroscopic, photochemical, biochemical, immuno-
chemical, or chemical means. For example, useful labels
include radioactive isotopes, magnetic beads, metallic
beads, colloidal particles, fluorescent dyes, electron-dense
reagents, enzymes (for example, as commonly used in an
ELISA), biotin, digoxigenin, or haptens.

By "disease" is meant any condition or disorder that
damages or interferes with the normal function of a cell,
tissue, or organ. In one embodiment, the disease is a
metabolic or neurological disease or disorder.

By "effective amount" is meant the amount required to
ameliorate the symptoms of a disease relative to an untreated
patient. The effective amount of active compound(s) used to
practice the present invention for therapeutic treatment of a
disease varies depending upon the manner of administration,
the age, body weight, and general health of the subject.
Ultimately, the attending physician or veterinarian will
decide the appropriate amount and dosage regimen. Such
amount is referred to as an "effective" amount. In one
embodiment, an effective amount is the amount that
enhances engraftment of a transplanted cell in the brain.

"Exogenous nucleic acid molecule" as used herein, refers
to a nucleic acid molecule that is not an endogenous nucleic
acid molecule, i.e., it is a nucleic acid molecule that does not
naturally occur in a cell.

By "fragment" is meant a portion of a protein or nucleic
acid that is substantially identical to a reference protein or
nucleic acid. In some embodiments the portion retains at
least 50%, 75%, or 80%, or more preferably 90%, 95%, or
even 99% of the biological activity of the reference protein
or nucleic acid described herein.

By "hematopoietic stem and progenitor cell (HSPC)" is
meant a stem cell or progenitor cell thereof that gives rise to
circulating and tissue resident hematopoietic cells in a
process known as hematopoiesis.

"Hybridization" means hydrogen bonding, which may be Watson-Crick, Hoogsteen or reversed Hoogsteen hydrogen bonding, between complementary nucleobases. For example, adenine and thymine are complementary nucleobases that pair through the formation of hydrogen bonds.

The terms "isolated," "purified," or "biologically pure" refer to material that is free to varying degrees from components which normally accompany it as found in its native state. "Isolate" denotes a degree of separation from original source or surroundings. "Purify" denotes a degree of separation that is higher than isolation. A "purified" or "biologically pure" protein is sufficiently free of other materials such that any impurities do not materially affect the biological properties of the protein or cause other adverse consequences. That is, a nucleic acid or peptide of this invention is purified if it is substantially free of cellular material, viral material, or culture medium when produced by recombinant DNA techniques, or chemical precursors or other chemicals when chemically synthesized. Purity and homogeneity are typically determined using analytical chemistry techniques, for example, polyacrylamide gel electrophoresis or high-performance liquid chromatography. The term "purified" can denote that a nucleic acid or protein gives rise to essentially one band in an electrophoretic gel. For a protein that can be subjected to modifications, for example, phosphorylation or glycosylation, different modifications may give rise to different isolated proteins, which can be separately purified.

By "isolated polynucleotide" is meant a nucleic acid (e.g., a DNA) that is free of the genes which, in the naturally-occurring genome of the organism from which the nucleic acid molecule of the invention is derived, flank the gene. The term therefore includes, for example, a recombinant DNA that is incorporated into a vector; into an autonomously replicating plasmid or virus; or into the genomic DNA of a prokaryote or eukaryote; or that exists as a separate molecule (for example, a cDNA or a genomic or cDNA fragment produced by PCR or restriction endonuclease digestion) independent of other sequences. In addition, the term includes an RNA molecule that is transcribed from a DNA molecule, as well as a recombinant DNA that is part of a hybrid gene encoding additional polypeptide sequence.

By an "isolated polypeptide" is meant a polypeptide of the invention that has been separated from components that naturally accompany it. Typically, the polypeptide is isolated when it is at least 60%, by weight, free from the proteins and naturally-occurring organic molecules with which it is naturally associated. Preferably, the preparation is at least 75%, more preferably at least 90%, and most preferably at least 99%, by weight, a polypeptide of the invention. An isolated polypeptide of the invention may be obtained, for example, by extraction from a natural source, by expression of a recombinant nucleic acid encoding such a polypeptide; or by chemically synthesizing the protein. Purity can be measured by any appropriate method, for example, column chromatography, polyacrylamide gel electrophoresis, or by HPLC analysis.

By "marker" is meant any protein or polynucleotide having an alteration in expression level or activity that is associated with a disease or disorder.

By "microglia" is meant an immune cell of the central nervous system.

As used herein, "obtaining" as in "obtaining an agent" includes synthesizing, purchasing, or otherwise acquiring the agent.

As used herein, the terms "prevent," "preventing," "prevention," "prophylactic treatment," and the like refer to reducing the probability of developing a disorder or condition in a subject who does not have, but is at risk of or susceptible to developing, a disorder or condition.

By "reduces" is meant a negative alteration of at least 10%, 25%, 50%, 75%, or 100%.

By "reference" is meant a standard or control condition.

A "reference sequence" is a defined sequence used as a basis for sequence comparison. A reference sequence may be a subset of or the entirety of a specified sequence; for example, a segment of a full-length cDNA or gene sequence, or the complete cDNA or gene sequence. For polypeptides, the length of the reference polypeptide sequence will generally be, in some embodiments at least about 16 amino acids, at least about 20 amino acids, at least about 25 amino acids, or about 35 amino acids, about 50 amino acids, or about 100 amino acids, or any integer thereabout or therebetween. For nucleic acids, the length of the reference nucleic acid sequence will generally be at least about 50 nucleotides, at least about 60 nucleotides, at least about 75 nucleotides, at least about 100 nucleotides, or at least about 300 nucleotides, or any integer thereabout or therebetween.

Nucleic acid molecules useful in the methods of the invention include any nucleic acid molecule that encodes a polypeptide of the invention or a fragment thereof. Such nucleic acid molecules need not be 100% identical with an endogenous nucleic acid sequence, but will typically exhibit substantial identity. Polynucleotides having "substantial identity" to an endogenous sequence are typically capable of hybridizing with at least one strand of a double-stranded nucleic acid molecule. Nucleic acid molecules useful in the methods of the invention include any nucleic acid molecule that encodes a polypeptide of the invention or a fragment thereof. Such nucleic acid molecules need not be 100% identical with an endogenous nucleic acid sequence, but will typically exhibit substantial identity. Polynucleotides having "substantial identity" to an endogenous sequence are typically capable of hybridizing with at least one strand of a double-stranded nucleic acid molecule. By "hybridize" is meant pair to form a double-stranded molecule between complementary polynucleotide sequences (e.g., a gene described herein), or portions thereof, under various conditions of stringency. (See, e.g., Wahl, G. M. and S. L. Berger (1987) Methods Enzymol. 152:399; Kimmel, A. R. (1987) Methods Enzymol. 152:507).

For example, stringent salt concentration will ordinarily be less than about 750 mM NaCl and 75 mM trisodium citrate, less than about 500 mM NaCl and 50 mM trisodium citrate, or about 250 mM NaCl and 25 mM trisodium citrate. Low stringency hybridization can be obtained in the absence of organic solvent, e.g., formamide, while high stringency hybridization can be obtained in the presence of at least about 35% formamide, and in some embodiments, at least about 50% formamide. Stringent temperature conditions will ordinarily include temperatures of at least about 30° C. at least about 37° C., or at least about 42° C. Varying additional parameters, such as hybridization time, the concentration of detergent, e.g., sodium dodecyl sulfate (SDS), and the inclusion or exclusion of carrier DNA, are well known to those skilled in the art. Various levels of stringency are accomplished by combining these various conditions as needed. In one embodiment, hybridization will occur at 30° C. in 750 mM NaCl, 75 mM trisodium citrate, and 1% SDS. In another embodiment, hybridization will occur at 37° C. in 500 mM NaCl, 50 mM trisodium citrate, 1% SDS, 35% formamide, and 100 μg/ml denatured salmon sperm DNA (ssDNA). In yet another embodiment, hybridization will occur at 42° C. in 250 mM NaCl, 25 mM trisodium citrate, 1% SDS, 50% formamide, and 200 µg/ml ssDNA. Useful variations on these conditions will be readily apparent to those skilled in the art.

For most applications, washing steps that follow hybridization will also vary in stringency. Wash stringency conditions can be defined by salt concentration and by temperature. As above, wash stringency can be increased by decreasing salt concentration or by increasing temperature. For example, stringent salt concentration for the wash steps will comprise less than about 30 mM NaCl and 3 mM trisodium citrate or less than about 15 mM NaCl and 1.5 mM trisodium citrate. Stringent temperature conditions for the wash steps will ordinarily include a temperature of at least about 25° C., at least about 42° C., or at least about 68° C. In some embodiments, wash steps will occur at 25° C. in 30 mM NaCl, 3 mM trisodium citrate, and 0.1% SDS. In other embodiments, wash steps will occur at 42 C in 15 mM NaCl, 1.5 mM trisodium citrate, and 0.1% SDS. In other embodiments, wash steps will occur at 68° C. in 15 mM NaCl, 1.5 mM trisodium citrate, and 0.1% SDS. Additional variations on these conditions will be readily apparent to those skilled in the art. Hybridization techniques are well known to those skilled in the art and are described, for example, in Benton and Davis (Science 196:180, 1977); Grunstein and Hogness (Proc. Natl. Acad. Sci., USA 72:3961, 1975); Ausubel et al. (Current Protocols in Molecular Biology, Wiley Interscience, New York, 2001); Berger and Kimmel (Guide to Molecular Cloning Techniques, 1987, Academic Press, New York); and Sambrook et al., Molecular Cloning: A Laboratory Manual, Cold Spring Harbor Laboratory Press, New York.

By "subject" is meant a mammal including, but not limited to, a human or a non-human mammal, such as a bovine, equine, canine, ovine, or feline.

By "substantially identical" is meant a polypeptide or nucleic acid molecule exhibiting at least 50% identity to a reference amino acid sequence (for example, any one of the amino acid sequences described herein) or nucleic acid sequence (for example, any one of the nucleic acid sequences described herein). In some embodiments, such a sequence is at least 60%, 80% or 85%, 90%, 95% or even 99% identical at the amino acid level or nucleic acid to the sequence used for comparison.

Sequence identity is typically measured using sequence analysis software (for example, Sequence Analysis Software Package of the Genetics Computer Group, University of Wisconsin Biotechnology Center, 1710 University Avenue, Madison, Wis. 53705, BLAST, BESTFIT, GAP, or PILEUP/PRETTYBOX programs). Such software matches identical or similar sequences by assigning degrees of homology to various substitutions, deletions, and/or other modifications. Conservative substitutions typically include substitutions within the following groups: glycine, alanine; valine, isoleucine, leucine; aspartic acid, glutamic acid; asparagine, glutamine; serine, threonine; lysine, arginine; and phenylalanine, tyrosine. In an exemplary approach to determining the degree of identity, a BLAST program may be used, with a probability score between $e^{-3}$ and $e^{-100}$ indicating a closely related sequence.

By "transgene" is meant an exogenous nucleic acid molecule, introduced into a host cell, that encodes a polypeptide or polynucleotide to be expressed in the host cell.

As used herein, the terms "treat," "treating," "treatment," and the like refer to reducing or ameliorating a disorder and/or symptoms associated therewith. It will be appreciated that, although not precluded, treating a disorder or condition does not require that the disorder, condition, or symptoms associated therewith be completely eliminated.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

Unless specifically stated or obvious from context, as used herein, the term "or" is understood to be inclusive. Unless specifically stated or obvious from context, as used herein, the terms "a", "an", and "the" are understood to be singular or plural.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

The recitation of a listing of chemical groups in any definition of a variable herein includes definitions of that variable as any single group or combination of listed groups. The recitation of an embodiment for a variable or aspect herein includes that embodiment as any single embodiment or in combination with any other embodiments or portions thereof.

Any compositions or methods provided herein can be combined with one or more of any of the other compositions and methods provided herein.

BRIEF DESCRIPTION OF THE DRAWINGS

FIG. 1A is a schematic diagram illustrating the protocol for transplantation (Tpx) of $CX3CR1^{+/GFP}$ or wild type (WT) total bone marrow (tBM) cells, containing hematopoietic stem progenitor cells (HSPCs), into recipient mice pretreated with a myeloablative regimen based on a 25 mg/kg daily dose of busulfan administered for 4 consecutive days. FIG. 1B is a graph showing the engraftment of the transplanted CD45.2 cells within bone marrow (BM) mononuclear cells (MNCs), expressed as ratio of $CD45.2^+$ cells to bone marrow mononuclear cells (BM MNCs), at 45, 90, and 180 days post-transplantation. FIG. 1C is a graph showing the frequency Lineage negative ($Lin^-$) HSPCs within total $CD45.2^+$ BM cells at 45, 90, and 180 days post-transplantation. FIG. 1D is a graph showing the frequency of $Kit^+/Sca-1^+/Lin^-$ (KLS) cells within $CD45.2^+$ total BM cells at 45, 90, and 180 days post-transplantation. FIG. 1E is a graph showing the engraftment of the transplanted CD45.2 cells within brain myeloid $CD11b^+$ cells, expressed as ratio of $CD45.2^+$ cells to total brain $CD11b^+$ cells, at 45, 90, and 180 days post-transplantation. FIG. 1F is a graph showing the frequency of mature microglia-like (µ) cells (identified as $CD11b^{high} CD45^{low}$ cells) within $CD45.2^+$ brain cells at 45, 90, and 180 days post-transplantation. FIG. 1G is a graph showing the frequency of transiently amplifying µ (TAµ) cells (identified as $CD11b^{low} CD45^{high}$ cells) within $CD45.2^+$ brain cells at 45, 90, and 180 days post-transplantation. As used in the figures, HCT denotes hematopoietic cell transplantation.

FIG. 2A is a schematic diagram illustrating the protocol for transplantation (Tpx) $CX3CR1^{+/GFP}$ and WT Lin$^-$ HSPCs into mice pretreated with a myeloablative regimen based on a 25 mg/kg daily dose of busulfan administered for 4 consecutive days. FIG. 2B is a graph showing the engraftment of the transplanted CD45.2 cells within bone marrow (BM) mononuclear cells (MNCs), expressed as ratio of CD45.2$^+$ cells to bone marrow mononuclear cells (BM MNCs), at 45, 90, and 180 days post-transplantation. FIG. 2C is a graph showing the frequency of Lineage negative (Lin$^-$) HSPCs within total CD45.2$^+$ BM cells at 45, 90, and 180 days post-transplantation. FIG. 2D is a graph showing the frequency of Kit$^+$/ Sca-1$^+$/Lin$^-$ (KLS) cells within CD45.2$^+$ total BM cells at 45, 90, and 180 days post-transplantation. FIG. 2E is a graph showing the engraftment of the transplanted CD45.2 cells within brain myeloid CD11b$^+$ cells, expressed as ratio of CD45.2$^+$ cells to total brain CD11b$^+$ cells, at 45, 90, and 180 days post-transplantation. FIG. 2F is a graph showing the frequency of mature microglia-like (0 cells (identified as CD11b$^{high}$ CD45$^{low}$ cells) within CD45.2$^+$ brain cells at 45, 90, and 180 days post-transplantation. FIG. 2G is a graph showing the frequency of transiently amplifying µ (TAµ) cells (identified as CD11b$^{low}$ CD45$^{high}$ cells) within CD45.2$^+$ brain cells at 45, 90, and 180 days post-transplantation. As used in the figures, HCT denotes hematopoietic cell transplantation.

FIG. 3A is a schematic diagram showing the protocol and timeline for intravenously (IV) and intracerebral ventricularly (ICV) competitive transplantation of wild type and $CX3CR1^{+/GFP}$ HSPCs transduced with lentiviral vectors to express different markers (Cherry and Blue Fluorescent Protein (BFP), respectively) into recipient mice pretreated with a myeloablative regimen based on a 25 mg/kg daily dose of busulfan administered for 4 consecutive days. The wild type and $CX3CR1^{+/GFP}$ HSPCs are transplanted at a 1:1 ratio in competitive transplant recipients (C+B denotes mice transplanted with 0.5×10$^6$ WT HSPCs+0.5×10$^6$ $CX3CR1^{+/GFP}$ HSPCs in the IV setting, 0.15×10$^6$ WT HSPCs+0.15×10$^6$ $CX3CR1^{+/GFP}$ HSPCs in the ICV setting). Control animals: Cherry=mice transplanted with only 1×10$^6$ WT HSPCs IV, 0.3×10$^6$ WT HSPCs ICV, BFP=mice transplanted with only 1×10$^6$ $CX3CR1^{+/GFP}$ HSPCs IV, 0.3×10$^6$ $CX3CR1^{+/GFP}$ HSPCs ICV. FIG. 3B is a graph showing the engraftment of the IV transplanted CD45.2 cells within hematopoietic organs (bone marrow (BM), Spleen, Thymus) of recipients, expressed as percentage of CD45.2+ donor cells. FIG. 3C is a graph characterizing donor cell composition as a percentage of marker-positive cells (Cherry$^+$ and BFP$^+$) within CD45.2$^+$ donor cells in hematopoietic organs of IV competitively transplanted mice. FIG. 3D is a graph characterizing BM donor cell composition of IV competitively transplanted mice as a percentage of marker-positive cells (Cherry$^+$ and BFP$^+$) assessed within myeloid (Gr-1+, cd11b+) and lymphoid (B220+ and CD3+) donor engrafted cells. FIG. 3E is a graph characterizing Spleen donor cell composition of IV competitively transplanted mice as a percentage of marker-positive cells (Cherry$^+$ and BFP$^+$) assessed within myeloid (Gr-1+, cd11b+) and lymphoid (B220+ and CD3+) donor engrafted cells. FIG. 3F is a graph showing the myeloid engraftment of the IV and ICV transplanted CD45.2 cells within brain of recipients, expressed as the ratio of CD45.2$^+$ donor cells to total CD11b$^+$ cells. FIG. 3G is a graph characterizing brain donor cell composition of the IV and ICV competitively transplanted mice as a percentage of marker-positive cells (Cherry$^+$ and BFP$^+$) within CD45.2$^+$ cd11b+ cells.

FIGS. 4A-4II shows the characterization of the brain myeloid progeny of $CX3CR1^{+/GFP}$ and WT HSPCs transplanted IV or ICV in the competitive transplant recipients described in FIGS. 3A-3G and sacrificed at 45 days post-transplant. FIG. 4A is an immunofluorescence image showing $CX3CR1^{+/GFP}$ and WT microglia-like cells engrafted in the brain of competitive transplanted mice. FIG. 4B shows the Macro workflow for branching cell analysis. Confocal images, after maximum intensity projection, were analyzed with a standardized Macro through ImageJ software. To characterize donor derived microglia cells, morphological criteria including threshold, skeleton, and removal of cell body was analyzed on each cell. FIG. 4C is a graph showing cumulative length of branches for the marker-positive myeloid progeny of IV- and ICV-delivered $CX3CR1^{+/GFP}$ (BFP) and WT (Cherry) cells in the brain of the competitive transplant recipients. FIG. 4D is a graph illustrating the complexity index calculated for the marker-positive myeloid progeny of IV- and ICV-delivered $CX3CR1^{+/GFP}$ (BFP) and WT (Cherry) cells in HSPC competitive transplant recipients. FIG. 4E is a graph depicting covered environmental area for the marker-positive myeloid progeny of IV- and ICV-delivered $CX3CR1^{+/GFP}$ (BFP) and WT (Cherry) cells in the brain of the competitive transplant recipients. FIG. 4F is an example of Sholl Analysis on a microglia-like cells analyzed via ImageJ software. FIG. 4G is a graph showing the results of a Scholl analysis applied to the marker-positive myeloid progeny of IV-delivered $CX3CR1^{+/GFP}$ (BFP) and WT (Cherry) cells in the brain of the competitive transplant recipients. FIG. 4H is a graph showing the results of a Scholl analysis applied to the marker-positive myeloid progeny of ICV-delivered $CX3CR1^{+/GFP}$ (BFP) and WT (Cherry) cells in the brain of the competitive transplant recipients.

FIG. 6A is a schematic diagram showing the protocol and timeline for competitive transplantation of wild type and $CX3CR1^{GFP/GFP}$ HSPCs transduced with lentiviral vectors to express different markers (Cherry and Blue Fluorescent Protein (BFP), respectively) into recipient mice pretreated with a myeloablative regimen based on a 25 mg/kg daily dose of busulfan administered for 4 consecutive days. The wild type and $CX3CR1^{GFP/GFP}$ HSPCs are transplanted at a 1:1 ratio in competitive transplant recipients (C+B denotes mice transplanted with 0.5×10$^6$ WT HSPCs+ 0.5×10$^6$ $CX3CR1^{GFP/GFP}$ HSPCs). Control animals: Cherry=mice transplanted with only 1×10$^6$ WT HSPCs, BFP=mice transplanted with only 1×10$^6$ $CX3CR1^{GFP/GFP}$ HSPCs. FIG. 6B is a graph showing the engraftment of the IV transplanted CD45.2 cells within hematopoietic organs (Peripheral Blood, BM and Spleen), expressed as percentage of CD45.2$^+$ cells. FIG. 6C is a graph showing the myeloid engraftment of the IV transplanted CD45.2 cells within brain of recipients, expressed as the ratio of CD45.2$^+$ donor cells to total CD11b$^+$ cells. FIG. 6D is a graph characterizing donor cell composition as a percentage of marker-positive cells (Cherry$^+$ and BFP$^+$) within CD45.2$^+$ donor cells in hematopoietic organs and brain of competitively transplanted recipients. FIG. 6E is a graph characterizing BM donor cell composition of competitively transplanted mice as a percentage of marker-positive cells (Cherry$^+$ and BFP$^+$) assessed within myeloid (Gr-1+, cd11b+) and lymphoid (B220+ and CD3+) donor engrafted cells. FIG. 6F is a graph characterizing Spleen donor cell composition of IV competitively transplanted mice as a percentage of marker-positive cells (Cherry$^+$ and BFP$^+$) assessed within myeloid (Gr-1+, cd11b+) and lymphoid (B220+ and CD3+) donor engrafted cells.

DETAILED DESCRIPTION OF THE INVENTION

Figure 1A:
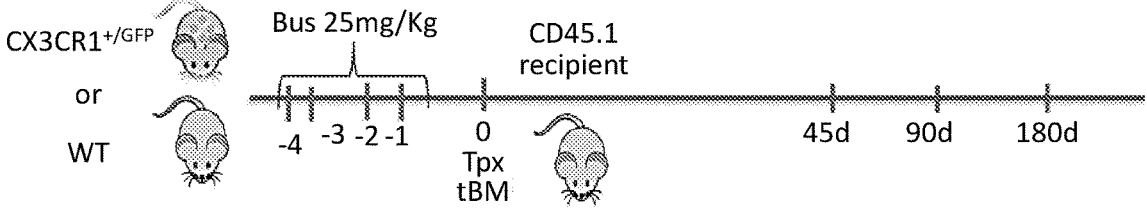
FIGS. 1A-1G illustrate the engraftment of $CX3CR1^{+/GFP}$ and wildtype (WT) cells in total bone marrow recipients.

This disclosure features compositions and methods that are useful for enhancing hematopoietic stem progenitor cell (HSPC) engraftment and the expansion of HSPC progeny.

This disclosure is based, at least in part, on the discovery that cells hemizygous for C-X3-C Motif Chemokine Receptor 1 (CX3CR1) generate a myeloid progeny and mature more quickly post-transplantation in a subject's brain than do wild-type cells.

CX3CR1

CX3CR1, also known as the fractalkine receptor, is a seven-transmembrane domain receptor belonging to the G protein-coupled receptor (GPCR) family. It is expressed in several cell types (e.g., microglia, monocytes, natural killer cells, T cells, and smooth muscle cells). Microglia cells are the only type of cell in the central nervous system that express CX3CR1. CX3CR1 is highly expressed during development and in response to brain damage/pathology.

Being a GPCR, CX3CR1's role is inhibitory as it acts to reduce production of cyclic adenosine monophosphate (cAMP) and prevent the triggering of subsequent signaling cascades mediated by second messengers. The intracellular pathways controlled by CX3CR1 signaling involve mainly phospholipase C (PLC), Phosphoinositide 3-kinase (PI3K), and extracellular-signal-regulated kinase (ERK) regulation, which modulate cell migration, adhesion, proliferation, and survival. Moreover, CX3CR1 is one of the key molecules involved in microglia ontogeny.

Fractalkine (CX3CL1) is the unique ligand for the chemokine receptor CX3CR1 and is expressed either as membrane-bound molecule or in a soluble form. Fractalkine cleavage is mediated by at least two enzymes, ADAM10 and ADAM17, which are active in homeostatic and inflammatory conditions, respectively. Fractalkine acts mainly as adhesion molecule in its membrane-bound form, while it has chemotactic properties towards CX3CR1 in its soluble form. Local production and membrane expression of CX3CL1 and also CX3CR1 are controlled by other cytokines, like TNFα, IL-1, IFNγ, NO, and hypoxia.

Activation of the CX3CR1-CX3CL1 axis leads to maintenance of microglia in a quiescent state and of homeostasis in the neuronal network. Under physiological conditions, CX3CL1 seems to inhibit microglial activation, while in particular conditions a paradoxical promotion of an inflammatory response may occur. Neurons are the greater producers of CX3CL1 in the brain and this axis is important for communication with microglia cells.

Surprisingly, as reported herein below, transplantation of total bone marrow or HSPCs from donor mice haploinsufficient for the CX3CR1 gene resulted in the generation of microglia like donor cell progeny in the recipients' brain that are more mature (enriched in CD11b$^{high}$ CD45$^{low}$ microglia-like, μ cells, versus CD11b$^{low}$ CD45$^{high}$ transiently amplifying, TAμ cells) than the brain cell progeny of standard wild type donor cells. This phenomenon resulted in an unexpected increase in the number of CX3CR1 hemizygous cells within CD11b$^{high}$ CD45$^{low}$ microglia-like μ cells within the transplanted cell progeny. This was paralleled by an increased number of KLS cells within donor BM cells of CX3CR1 haploinsufficient cell transplant recipients, as compared to KLS cell number within donor BM cells of WT cell transplant recipients.

Unexpectedly, in the context of competitive transplantation, CX3CR1 haplo-insufficient donor derived cells contributed to a greater extent as compared to wild type donor cells to the repopulation of the hematopoietic organs and of the brain myeloid compartment of the recipients. In each tested tissue and cell compartment, the frequency of CX3CR1 haplo-insufficient cells was greater than the frequency of WT cells. A branching study performed on the engrafted cells showed that the brain myeloid progeny of CX3CR1$^{+/GFP}$ cells also acquire a more mature microglia-like morphology and express microglia-associated genes at higher levels than the WT cell progeny.

Of note, CX3CR1 hemizygous mice have no obvious phenotype. Thus, there was no reason to expect that the transplant of CX3CR1 hemizygous cells would differ from the transplant of wild type cells.

Thus, the present disclosure provides a CX3CR1 hemizygous or homozygous defective HSPC cell for use in transplantation. In some embodiments, the CX3CR1 hemizygous or homozygous defective cell is a hematopoietic stem progenitor cell (HSPC). In some embodiments, the CX3CR1 hemizygous or homozygous defective cell is isolated from a biological sample or is generated via genome editing, targeted gene addition, or using any other method known in the art to knock out a gene. Methods for collecting biological samples and isolating cells (e.g., HSPCs) therefrom are well-known in the art. In some embodiments, the cells are assessed to determine immunocompatability with a subject.

Expression of Therapeutic Agents

Some aspects of the present invention provide a CX3CR1 hemizygous or homozygous defective cell comprising an exogenous nucleic acid molecule encoding a therapeutic agent (e.g., therapeutic polypeptide or polynucleotide). The therapeutic agent, in some embodiments, is a polynucleotide or a polypeptide. In some embodiments, the polypeptide or polynucleotide may ameliorate a disease (e.g., a neurological or metabolic disease or disorder) or symptom thereof. In some embodiments the nucleic acid molecule encoding the therapeutic agent is integrated into the genome of the CX3CR1 hemizygous or homozygous defective cell. In some embodiments, the nucleic acid molecule encoding the therapeutic agent is inserted into the loci of the missing or disabled CX3CR1 allele. In some embodiments, expression of the exogenous nucleic acid molecule is regulated by the CX3CR1 promoter/enhancer region, consistent with CX3CR1 expression.

The exogenous nucleic acid molecule, in some embodiments, comprises regulatory elements for expressing a transgene. For example, an exogenous nucleic acid molecule may comprise a transgene encoding a therapeutic agent for the treatment of a metabolic and neurological disease and, in some instances, a promoter for expressing the transgene. In some embodiments, the promoter is a constitutively active promoter such as, for example, the cytomegalovirus (CMV) or simian virus 40 (SV40) promoter. In some embodiments, the promoter may be a tissue-specific promoter, wherein the transgene is expressed upon engraftment and differentiation of the HSPC. In some embodiments, a neuronal specific promoter is the synapsin (Syn) promoter. In some embodiments, the promoter is an inducible promoter, wherein the transgene is expressed only in the presence or absence of a particular compound. For example, tetracycline is a drug that can be used to activate a tetracycline-sensitive promoter. In some embodiments, microglial or microglial-like cells derived from an HSPC comprising a transgene driven by a brain-specific promoter transplanted into the brain of a subject will express the transgene.

In some embodiments, the exogenous nucleic acid molecule may comprise, in addition to a transgene, a detectable label or other marker that allows identification of cells that have been successfully modified or that are derived from cells that have been successfully modified to express the transgene.

Generation of Hemizygous or Homozygous Defective CX3CR1 Cells

In some embodiments of the present disclosure, an HSPC is edited to remove or otherwise disable one or both functional copies of CX3CR1 to generate HSPCs that are hemizygous or homozygous defective for the gene.

Gene editing is a major focus of biomedical research, embracing the interface between basic and clinical science. "Gene editing" tools can manipulate a cell's DNA sequence at a specific chromosomal locus without introducing mutations at other sites of the genome. This technology effectively enables a researcher to manipulate the genome of a cell in vitro or in vivo.

In one embodiment, gene editing involves targeting an endonuclease to a specific site in a genome to generate a double strand break at the specific location. If a donor DNA molecule (e.g., a plasmid or oligonucleotide) is introduced, interactions between the nucleic acid comprising the double strand break and the introduced DNA can occur, especially if the two nucleic acids share homologous sequences. In this instance, a process termed "gene targeting" can occur, in which the DNA ends of the chromosome invade homologous sequences of the donor DNA by homologous recombination. By using the donor plasmid sequence as a template for homologous recombination, a seamless knock out of the gene of interest can be accomplished. Importantly, if the donor DNA molecule includes a deletion within the target gene (e.g., CX3CR1), homologous recombination-mediated double strand break repair will introduce the donor sequence into the chromosome, resulting in the deletion being introduced within the chromosomal locus. By targeting the nuclease to a genomic site that contains the target gene, the concept is to use double strand break formation to stimulate homologous recombination and to thereby replace the functional target gene with a deleted form of the gene. The advantage of the homologous recombination pathway is that it has the potential to generate seamlessly a knockout of the gene in place of the previous wild-type allele.

Genome editing tools may use double strand breaks to enhance gene manipulation of cells. Such methods can employ zinc finger nucleases, described for example in U.S. Pat. Nos. 6,534,261; 6,607,882; 6,746,838; 6,794,136; 6,824,978; 6,866,997; 6,933,113; 6,979,539; 7,013,219; 7,030,215; 7,220,719; 7,241,573; 7,241,574; 7,585,849; 7,595,376; 6,903,185; and 6,479,626; and U.S. Pat. Publ. Nos. 20030232410 and US2009020314, which are incorporated herein by reference); Transcription Activator-Like Effector Nucleases (TALENs; described for example in U.S. Pat. Nos. 8,440,431; 8,440,432; 8,450,471; 8,586,363; and 8,697,853; and U.S. Pat. Publ. Nos. 20110145940; 20120178131; 20120178169; 20120214228; 20130122581; 20140335592; and 20140335618; which are incorporated herein by reference), and the CRISPR (Clustered Regularly Interspaced Short Palindromic Repeats)/Cas9 system (described for example in U.S. Pat. Nos. 8,697,359; 8,771,945; 8,795,965; 8,871,445; 8,889,356; 8,906,616; 8,932,814; 8,945,839; 8,993,233; and 8,999,641; and U.S. Pat. Publ. Nos. 20140170753; 20140227787; 20140179006; 20140189896; 20140273231; 20140242664; 20140273232; 20150184139; 20150203872; 20150031134; 20150079681; 20150232882; and 20150247150, which are incorporated herein by reference). For example, zinc finger nuclease DNA sequence recognition capabilities and specificity can be unpredictable. Similarly, TALENs and CRISPR/Cas9 cleave not only at the desired site, but often at other "off-target" sites, as well. These methods have significant issues connected with off-target double-stranded break induction and the potential for deleterious mutations, including indels, genomic rearrangements, and chromosomal rearrangements, associated with these off-target effects. Zinc finger nucleases and TALENs entail use of modular sequence-specific DNA binding proteins to generate specificity for about 18 bases sequences in the genome.

RNA-guided nuclease-mediated genome editing, based on Type 2 CRISPR (Clustered Regularly Interspaced Short Palindromic Repeat)/Cas (CRISPR Associated) systems, offers a valuable approach to alter the genome. In brief, Cas9, a nuclease guided by single-guide RNA (sgRNA), binds to a targeted genomic locus next to the protospacer adjacent motif (PAM) and generates a double-strand break. The double-strand break is then repaired either by non-homologous end joining, which leads to insertion/deletion (indel) mutations, or by homology-directed repair, which requires an exogenous template and can generate a precise modification at a target locus (Mali et al., Science, Feb. 15, 2013; 339 (6121): 823-6, the contents of which are herein by reference in their entirety). Unlike gene therapy methods that add a functional, or partially functional, copy of a gene to a subject's cells, but retain the original dysfunctional copy of the gene, this system can remove the defect in the dysfunctional copy. Genetic correction using modified nucleases has been demonstrated in tissue culture cells and rodent models of rare diseases.

CRISPR has been used in a wide range of organisms including baker's yeast (S. cerevisiae), zebra fish, nematodes (e.g., C. elegans), plants, mice, and several other organisms. Additionally, CRISPR has been modified to make programmable transcription factors that allow scientists to target and activate or silence specific genes. Libraries of tens of thousands of guide RNAs are now available. By inserting a plasmid containing cas genes and specifically designed CRISPRs, an organism's genome can be cut at any desired location.

CRISPR repeats range in size from 24 to 48 base pairs. They usually show some dyad symmetry, implying the formation of a secondary structure such as a hairpin, but are not truly palindromic. Repeats are separated by spacers of similar length, with some CRISPR spacer sequences exactly matching sequences from plasmids and phages, although some spacers match the prokaryote's genome (self-targeting spacers). New spacers can be added rapidly in response to phage infection.

CRISPR-associated (cas) genes are often associated with CRISPR repeat-spacer arrays. As of 2013, more than forty different Cas protein families had been described. Of these protein families, Cas1 appears to be ubiquitous among different CRISPR/Cas systems. Particular combinations of cas genes and repeat structures have been used to define eight CRISPR subtypes (Ecoli, Ypest, Nmeni, Dvulg, Tneap, Hmari, Apern, and Mtube), some of which are associated with an additional gene module encoding repeat-associated mysterious proteins (RAMPs). More than one CRISPR subtype may occur in a single genome. The sporadic distribution of the CRISPR/Cas subtypes suggests that the system is subject to horizontal gene transfer during microbial evolution.

Exogenous DNA is apparently processed by proteins encoded by Cas genes into small elements (about thirty base pairs in length), which are then inserted into the CRISPR locus near the leader sequence. RNAs from the CRISPR loci are constitutively expressed and are processed by Cas proteins to small RNAs comprising individual, exogenously-derived sequence elements with a flanking repeat sequence. The RNAs guide other Cas proteins to silence exogenous genetic elements at the RNA or DNA level. Evidence suggests functional diversity among CRISPR subtypes. The Cse (Cas subtype *E. coli*) proteins (called CasA-E in *E. coli*) form a functional complex, Cascade, that processes CRISPR RNA transcripts into spacer-repeat units that Cascade retains. In other prokaryotes, Cash processes CRISPR transcripts. Interestingly, CRISPR-based phage inactivation in *E. coli* requires Cascade and Cas3, but neither Cas1 nor Cas2. The Cmr (Cas RAMP module) proteins found in *Pyrococcus furiosus* and other prokaryotes form a functional complex with small CRISPR RNAs that recognizes and cleaves complementary target RNAs. RNA-guided CRISPR enzymes are classified as type V restriction enzymes. See also U.S. Patent Publication 2014/0068797, which is incorporated by reference in its entirety.

As an RNA guided protein, Cas9 requires an RNA molecule to direct the recognition of DNA targets. Though Cas9 preferentially interrogates DNA sequences containing a protospacer adjacent motif (PAM) sequence (i.e., NGG). However, the Cas9-gRNA complex requires a substantial complementarity between the guide RNA (gRNA) and the target nucleic acid sequence to create a double strand break. Synthetic gRNA can be designed to combine the essential RNA sequences for Cas9 targeting into a single RNA expressed with the RNA polymerase type 21 promoter U6 driving expression. Synthetic gRNAs are slightly over 100 bases at the minimum length and contain a portion which is targets the 20 protospacer nucleotides immediately preceding the PAM sequence NGG.

In one approach, one or more cells of a subject are altered to delete or inactivate CX3CR1 using a CRISPR-Cas system. Cas9 can be used to target a CX3CR1 gene. Upon target recognition, Cas9 induces double strand breaks in the CX3CR1 target gene. Homology-directed repair (HDR) at the double-strand break site can allow insertion of an inactive or deleted form of the CX3CR1 sequence.

The following US patents and patent publications are incorporated herein by reference: U.S. Pat. Nos. 8,697,351; 20140170753; 20140179006; 20140179770; 20140186843; 20140186958; 20140189896; 20140227787; 20140242664; 20140248702; 20140256046; 20140273230; 20140273233; 20140273234; 20140295556; 20140295557; 20140310830; 20140356956; 20140356959; 20140357530; 20150020223; 20150031132; 20150031133; 20150031134; 20150044191; 20150044192; 20150045546; 20150050699; 20150056705; 20150071898; 20150071899; 20150071903; 20150079681; 20150159172; 20150165054; 20150166980; and 20150184139. In some embodiments, editing the HSPC to generate hemizygous CX3C3R1 cells comprises inserting an exogenous nucleic acid molecule encoding a therapeutic agent at the CX3CR1 locus.

Expression of Therapeutic Agents in CX3CR1 Hemizygous or Homozygous Defective Cells Methods are provided herein to modify a CX3CR1 hemizygous or homozygous defective cell to express a therapeutic agent (e.g., neuroprotective polypeptide or polypeptide required to ameliorate a metabolic disorder). In some embodiments, the CX3CR1 cell is modified to incorporate an exogenous nucleic acid molecule encoding a therapeutic agent. The exogenous nucleic acid molecule may be incorporated into the genome of the CX3CR1 cell. The present disclosure also contemplates modifying a CX3CR1 hemizygous or homozygous defective HSPC to incorporate a nucleic acid sequence encoding a therapeutic agent in the missing CX3CR1 allele locus. In this way, the hemizygous or homozygous defective HSPCs are manipulated to express a therapeutic transgene under CX3CR1 locus control.

To express exogenous polynucleotides or polypeptides, nucleic acid molecules encoding the polynucleotides and polypeptides can be inserted into expression vectors by techniques known in the art. For example, double-stranded DNA can be cloned into a suitable vector by restriction enzyme linking involving the use of synthetic DNA linkers or by blunt-ended ligation. DNA ligases are usually used to ligate the DNA molecules and undesirable joining can be avoided by treatment with alkaline phosphatase.

The present disclosure also includes vectors (e.g., recombinant plasmids) that include nucleic acid molecules (e.g., transgenes) as described herein. The term "recombinant vector" includes a vector (e.g., plasmid, phage, phasmid, virus, cosmid, fosmid, or other purified nucleic acid vector) that has been altered, modified, or engineered such that it contains greater, fewer, or different nucleic acid sequences than those included in the native or natural nucleic acid molecule from which the recombinant vector was derived. For example, a recombinant vector may include a nucleotide sequence encoding a polypeptide, or fragment thereof, operatively linked to regulatory sequences such as promoter sequences, terminator sequences, long terminal repeats, untranslated regions, and the like, as defined herein. Recombinant expression vectors allow for expression of the genes or nucleic acids included in them.

In some embodiments of the present disclosure, one or more DNA molecule having a nucleotide sequence encoding one or more polypeptides or polynucleotides described herein are operatively linked to one or more regulatory sequences, which can integrate the desired DNA molecule into a eukaryotic cell. Cells (e.g., CX3CR1 hemizygous cells) that have been stably transfected or transduced by the introduced DNA can be selected, for example, by introducing one or more markers that allow for selection of host cells containing the expression vector. A selectable marker gene can either be linked directly to a nucleic acid sequence to be expressed or introduced into the same cell by co-transfection or co-transduction. Any additional elements needed for optimal synthesis of polynucleotides or polypeptides described herein would be apparent to one of ordinary skill in the art.

Methods of introducing exogenous nucleic acid molecules into a cell (e.g., CX3CR1 hemizygous cells) are known in the art. For example, eukaryotic cells can take up nucleic acid molecules from the environment via transfection (e.g., calcium phosphate-mediated transfection). Transfection does not employ a virus or viral vector for introducing the exogenous nucleic acid into the recipient cell. Stable transfection of a eukaryotic cell comprises integration into the recipient cell's genome of the transfected nucleic acid, which can then be inherited by the recipient cell's progeny.

Eukaryotic cells (i.e., CX3CR1 hemizygous or homozygous defective HSPCs) can be modified via transduction, in which a virus or viral vector stably introduces an exogenous nucleic acid molecule to the recipient cell. Eukaryotic transduction delivery systems are known in the art. Transduction of most cell types can be accomplished with retroviral, lentiviral, adenoviral, adeno-associated, and avian virus systems, and such systems are well-known in the art. While retroviruses systems are generally not compatible with neuronal cell transduction, lentiviruses are a genus of retroviruses well-suited for transducing stem cells as well as neuronal cells. Thus, in some embodiments of the present disclosure, the viral vector system is a lentiviral system. In some embodiments, the viral vector system is an avian virus system, for example, the avian viral vector system described in U.S. Pat. No. 8,642,570, DE102009021592, PCT/EP2010/056757, and EP2430167, the contents of which are incorporated herein by reference in their entirety. In some embodiments, the viral vectors are assembled or packaged in a packaging cell prior to contacting the intended recipient cell. In some embodiments, the vector system is a self-inactivating system, wherein the viral vector is assembled in a packaging cell, but after contacting the recipient cell, the viral vector is not able to be produced in the recipient cell.

The components of a viral vector are encoded on plasmids. Because efficiencies of transduction decrease with large plasmid size and to increase the safety of viral vectors (see e.g., Addgene.org/guides/lentivirus/), multiple plasmids that have different viral sequences may be necessary for packaging. For example, in a lentiviral vector system, a first plasmid may comprise a nucleotide sequence encoding a Group antigens (gag) and/or a reverse transcriptase (pol) gene, while a second plasmid encodes regulator of expression of virion proteins (rev) and/or envelope (env) genes. The exogenous nucleic acid molecule comprising a transgene can be packaged into the vector and delivered into a recipient cell where the transgene is integrated into the recipient cell's genome. Additionally, the transgene may be packaged using a split-packaging system as described in U.S. Pat. No. 8,642,570, DE102009021592, PCT/EP2010/056757, and EP2430167.

After the introduction of one or more vector(s), host cells are cultured prior to administration to a subject. Expression of recombinant proteins encoded in the vectors can be detected by immunoassays including Western blot analysis, immunoblot, and immunofluorescence. Purification of recombinant proteins can be carried out by any of the methods known in the art or described herein, for example, any conventional procedures involving extraction, precipitation, chromatography, and electrophoresis. A further purification procedure that may be used for purifying proteins is affinity chromatography using monoclonal antibodies, which bind a target protein. Generally, crude preparations containing a recombinant protein are passed through a column on which a suitable monoclonal antibody is immobilized. The protein usually binds to the column via the specific antibody while the impurities pass through. After washing the column, the protein is eluted from the gel, by changing pH or ionic strength, for example.

Hematopoietic Cell Transplantation

HSPCs and/or their progeny that are CX3CR1 hemizygous or homozygous defective can serve as vehicles for therapeutic molecule delivery across the blood brain barrier by contributing to the turnover of myeloid cell populations in the brain. Methods for hematopoietic cell transplantation (HCT) and hematopoietic stem cell (HSC)-based gene therapy are known in the art and have been used to treat patients affected by non-hematological and non-oncological diseases affecting the nervous system, such as peroxisomal disorders and lysosomal storage diseases (LSDs) (Cartier et al. Science 326, 818-823 (2009); Biffi et al. Science 341, 1233158 (2013); Sessa et al. Lancet 388, 476-487 (2016)) and neurological diseases (Simard et al. Neuron 49, 489-502 (2006)). Indeed, HSPCs and/or their progeny can contribute to the turnover of myeloid cell populations in the brain (Ajami et al. Nat Neurosci 10, 1538-1543 (2007); Ajami et al. Nat Neurosci 14, 1142-1149 (2011); Biffi et al. J. Clin. Invest. 116, 3070-3082 (2006); Mildner et al. Nat Neurosci 10, 1544-1553 (2007); Capotondo et al. Proc Natl Acad Sci USA. 109, 15018-15023 (2012). Microglia's role in the progression and outcomes of these disorders has been described (Jeyakumar et al. Brain 126, 974-987 (2003); Wada et al. Proc Natl Acad Sci USA 97, 10954-10959 (2000); Ohmi et al. Proc. Natl. Acad. Sci. USA 100, 1902-1907 (2003); Eichler et al. Ann Neurol 63, 729-742 (2008), the contents of each are incorporated herein in their entirety).

Despite microglia having a developmental origin distinct from that of bone marrow-derived myelomonocytes (Ginhoux et al. Science 330, 841-845 (2010), the contents of which are incorporated herein by reference in their entirety), it has recently been demonstrated that under specific experimental conditions, cells of donor origin showing a microglia-like phenotype and expressing some microglia surface markers could be successfully generated in the brain of mice transplanted with donor HSPCs. Transplant efficiency can be improved with an ablative preconditioning regimen to destroy endogenous microglia progenitors, such as that described in International Application No. PCT/US2017/056774, the contents of which are incorporated herein by reference in their entirety. In some embodiments of the present disclosure, the ablative conditioning regimen comprises administering an alkylating agent to a subject prior to transplantation. In some embodiments, the alkylating agent is busulfan. Busulfan is capable of ablating functionally-defined brain-resident microglia precursors (Capotondo et al. Proc Natl Acad Sci USA. 109, 15018-15023 (2012); Wilkinson et al. Mol Ther 21, 868-876 (2013)).

HSPCs have the capacity to generate new populations of myeloid and microglia cells that can exert therapeutic effects in the central nervous system (CNS). This disclosure provides compositions comprising CX3CR1 hemizygous or homozygous defective HSPCs and enhanced methods for engrafting such cells.

HSPC transplantation generates transcriptionally-dependable microglia through a stepwise process similar to physiological post-natal microglia maturation. CX3CR1 hemizygous or homozygous defective hematopoietic cells able to generate new microglia upon transplantation into myeloablated recipients are retained within human and murine long-term hematopoietic stem cells (HSCs). In some embodiments, microglia cells can be generated after intracerebroventricular delivery of CX3CR1 hemizygous or homozygous defective HSPCs, which unexpectedly results in faster and more widespread microglia replacement compared to delivery of wild-type HSPCs.

Pharmaceutical Compositions

Compositions contemplated in the present disclosure include pharmaceutical compositions comprising cells hemizygous or homozygous defective for CX3CR1. In some embodiments, the cells hemizygous for CX3CR1 are modified to express a therapeutic agent. In some embodiments, the cells homozygous for CX3CR1 (e.g., CX3CR1$^{GFP/GFP}$) are modified to express a therapeutic agent. In some embodiments, the therapeutic agent is neuroprotective or is required to replace a missing metabolic enzyme. The pharmaceutical compositions contemplated herein can comprise autogenic or allogenic cells. In some embodiments, the cells are CX3CR1 hemizygous or homozygous defective HSPCs.

The CX3CR1 hemizygous or homozygous defective HSPCs as described herein can be administered as therapeutic compositions (e.g., as pharmaceutical compositions). Cellular compositions as described herein can be provided as sterile liquid preparations, e.g., isotonic aqueous solutions, suspensions, emulsions, dispersions, or viscous compositions, which may be buffered to a selected pH. A liquid preparation may be easier to prepare than a gel, another viscous composition, or a solid composition. Additionally, a liquid composition may be more convenient to administer (i.e., by injection). Viscous compositions, on the other hand, can be formulated within the appropriate viscosity range to provide longer contact periods with specific tissues. Liquid or viscous compositions can comprise a carrier, which can be a solvent or dispersing medium comprising, for example, water, saline, phosphate buffered saline, polyol (e.g., glycerol, propylene glycol, liquid polyethylene glycol, and the like), and suitable mixtures thereof.

Sterile injectable solutions can be prepared by incorporating the cells described herein in a sufficient amount of an appropriate diluent. Such compositions may be in admixture with a suitable carrier or excipient such as sterile water, physiological saline, glucose, dextrose, or another carrier or excipient suitable for delivering live cells to a subject. The compositions can also be lyophilized. The compositions can contain auxiliary substances such as wetting, dispersing, or emulsifying agents (e.g., methylcellulose), pH buffering agents, gelling or viscosity enhancing additives, preservatives, flavoring agents, colors, and the like, depending upon the route of administration and the preparation desired. Standard texts, such as "Remington's Pharmaceutical Science," 17th edition, 1985, incorporated herein by reference, may be consulted to prepare suitable preparations, without undue experimentation.

Additives that enhance the stability and sterility of the cellular compositions, including antimicrobial preservatives, antioxidants, chelating agents, and buffers, can be added. Prevention of the action of microorganisms can be ensured by an antibacterial or antifungal agent including, but not limited to, parabens, chlorobutanol, phenol, and sorbic acid. According to the present disclosure, however, any vehicle, diluent, or additive used must be compatible with the cells.

The compositions can be isotonic, i.e., they have the same osmotic pressure as blood and cerebrospinal fluid. The desired isotonicity of the compositions of this invention may be accomplished using sodium chloride, or other pharmaceutically acceptable agents such as dextrose, boric acid, sodium tartrate, propylene glycol, or other inorganic or organic solutes. Sodium chloride may be suitable for buffers containing sodium ions.

Viscosity of the compositions, if desired, can be maintained at a selected level using a pharmaceutically acceptable thickening agent. In some embodiments, the thickening agent is methylcellulose, which is readily and economically available and is easy to work with. Other suitable thickening agents include, but are not limited to, xanthan gum, carboxymethyl cellulose, hydroxypropyl cellulose, and carbomer. The concentration of the thickener will depend upon the agent selected and the amount of the agent used. Suitable carriers and other additives may be chosen depending on the route of administration and the nature of the dosage form (e.g., a liquid dosage form can be formulated into a solution, a suspension, a gel, or another liquid form, such as a time release formulation or liquid-filled form).

An effective amount of cells to be administered can vary for the subject being treated. In one embodiment, between about $10^4$ to about $10^8$ cells, and in another embodiment between about $10^5$ to about $10^7$ cells are administered to a subject.

The skilled artisan can readily determine the amounts of CX3CR1 hemizygous or homozygous defective cells and optional additives, vehicles, and/or carrier in compositions to be administered. In one embodiment any additive (in addition to the cell(s)) is present in an amount of about 0.001% to about 50% (weight) solution in phosphate buffered saline, and the active ingredient is present in the order of micrograms to milligrams, such as about 0.0001% to about 5 wt %. In another embodiment, the active ingredient is present at about 0.0001% to about 1 wt %. In yet another embodiment, the active ingredient is present at about 0.0001% to about 0.05 wt %. In still other embodiments, the active ingredient is present at about 0.001% to about 20 wt %. In some embodiments, the active ingredient is present at about 0.01% to about 10 wt %. In another embodiment, the active ingredient is present at about 0.05% to about 5 wt %. For any composition to be administered to an animal or human, and for any particular method of administration, toxicity can be determined by measuring the lethal dose (LD) and LD$_{50}$ in a suitable animal model, e.g., a rodent such as mouse. The dosage of the composition(s), concentration of components therein, and timing of administering the composition(s), which elicit a suitable response can also be determined. Such determinations do not require undue experimentation in light of the knowledge of the skilled artisan, this disclosure, and the documents cited herein. The time for sequential administrations can also be ascertained without undue experimentation.

Methods of Treatment

The present disclosure provides methods of treatment for a subject in need thereof by administering a cell hemizygous or homozygous defective for CX3CR1, or a pharmaceutical composition comprising the cell, to the subject. In some embodiments, the subject in need of treatment has or is suspected of having a metabolic or neurological disease.

A health care professional may diagnose a subject as having a metabolic or neurological disease by the assessment of one or more symptoms of disease in the subject. The present disclosure provides methods of treating a metabolic or neurological disease or symptoms thereof that comprise administering to a subject (e.g., a mammal, such as a human) a therapeutically effective amount of a cell hemizygous for CX3CR1 that may or may not express a therapeutic polypeptide. In some embodiments, the cell is an HSPC. In some embodiments, the cell is a microglial progenitor cell. Thus, the method in some embodiments comprises administering to the subject a therapeutically effective amount of a cell described herein sufficient to treat a metabolic or neurological disease or symptom thereof, under such conditions that the disease is treated.

The methods herein include administering to the subject (including a subject identified as in need of such treatment) an effective amount of cells described herein, or a composition comprising such cells as described herein to produce such effect. Such treatment will be suitably administered to a subject, particularly a human, suffering from, having, susceptible to, or at risk for, a metabolic or neurological disease, or a symptom thereof. In some embodiments, the methods herein include administering to the subject (including a subject identified as in need of such treatment) an effective amount of a compound described herein, or a composition described herein to produce such effect.

In some embodiments, the cell or the composition comprising the cell is administered to a subject in a targeted manner. For example, in some embodiments, a composition comprising a cell hemizygous or homozygous defective for CX3CR1 is administered directly to a subject's brain. In some embodiments, the composition is delivered directly to the brain via intracerebroventricular administration. In some embodiments, the composition is delivered in this manner to the lateral ventricles of the subject's brain.

Alternatively, the composition may be delivered systemically, such as by intravenous administration. Cells administered in such a manner must traverse the blood brain barrier prior to engrafting in the subject's brain. Other modes of administration (parenteral, mucosal, implant, intraperitoneal, intradermal, transdermal, intramuscular, intracerebroventricular injection, intravenous including infusion and/or bolus injection, and subcutaneous) are generally known in the art. In some embodiments, cells are administered in a medium suitable for injection, such as phosphate buffered saline, into a subject. Because the cells being administered to the subject are intended to repopulate microglial cells, intracerebroventricular administration may be advantageous as other routes of administration require crossing the blood brain barrier.

In some embodiments, the cell hemizygous or homozygous defective for CX3CR1 is modified to express a therapeutic agent. In some embodiments, the genome of the cell hemizygous or homozygous defective for CX3CR1 is modified to have a nucleic acid encoding a therapeutic agent at the CX3CR1 locus, such that the cell comprises one functional copy of the CX3CR1 gene and one functional copy of the nucleic acid molecule encoding the therapeutic agent. In some embodiments, the therapeutic agent is a neuroprotective agent. In such embodiments, engraftment of transplanted CX3CR1 hemizygous or homozygous defective cells that express a therapeutic agent in a subject's brain provides a population of cells that express a therapeutic agent. But because the transplanted cells are meant to replace endogenous cells (i.e., microglial cells), in certain embodiments, methods of treating a subject having, susceptible to, or at risk of developing a metabolic or neurological disease further comprise administering to a subject prior to administering a CX3CR1 hemizygous or homozygous defective HSPC expressing a therapeutic agent, an agent for ablating endogenous cells, such as microglia. In some embodiments, the agent is an alkylating agent. In some embodiments, the alkylating agent is busulfan. In some embodiments, nanoparticle delivery of alkylating agents may be effective in creating a suitable environment for engraftment of transplanted HSPCs, as described in International Application No. PCT/US2017/056774, the contents of which are incorporated herein by reference in their entirety.

Kits

The present disclosure contemplates kits for the treatment or prevention of a metabolic or neurological disease. In some embodiments, the kit comprises a composition comprising a cell hemizygous or homozygous defective for CX3CR1. In some embodiments, the cell hemizygous or homozygous defective for CX3CR1 is modified to express a therapeutic agent. In some embodiments, the genome of a cell hemizygous defective for CX3CR1 is modified to have a nucleic acid encoding a therapeutic agent at the CX3CR1 locus, such that the cell comprises one functional copy of the CX3CR1 gene and one functional copy of the nucleic acid molecule encoding the therapeutic agent. In some embodiments, the genome of a cell homozygous defective for CX3CR1 is modified to have a nucleic acid encoding a therapeutic agent at the CX3CR1 locus, such that the cell comprises no functional copies of the CX3CR1 gene and at least one functional copy of the nucleic acid molecule encoding the therapeutic agent. The kit can include instructions for a treatment protocol, reagents, equipment (test tubes, reaction vessels, needles, syringes, etc.), and standards for calibrating or conducting the treatment protocol. The instructions provided in a kit according to the present disclosure may be directed to suitable operational parameters in the form of a detectable label or a separate insert. Optionally, the kit may further comprise a standard or control information so that the test sample can be compared with the control information standard to determine if a consistent result is achieved. In some embodiments, the kit includes a nanoparticle for ablative conditioning of endogenous microglial cells.

In some embodiments, the kit comprises a sterile container which contains a therapeutic or prophylactic cellular composition; such containers can be boxes, ampoules, bottles, vials, tubes, bags, pouches, blister-packs, or other suitable container forms known in the art. Such containers can be made of plastic, glass, laminated paper, metal foil, or other materials suitable for holding medicaments.

If desired, an agent of the invention is provided together with instructions for administering the agent to a subject having or at risk of developing a metabolic or neurological disease or disorder of the central nervous system. The instructions will generally include information about the use of the composition for the treatment or prevention of the disease or disorder. In other embodiments, the instructions include at least one of the following: description of the therapeutic agent; dosage schedule and administration for treatment or prevention of a neurological disease or symptoms thereof; precautions; warnings; indications; counterindications; overdosage information; adverse reactions; animal pharmacology; clinical studies; and/or references. The instructions may be printed directly on the container (when present), or as a label applied to the container, or as a separate sheet, pamphlet, card, or folder supplied in or with the container.

The practice of the present invention employs, unless otherwise indicated, conventional techniques of molecular biology (including recombinant techniques), microbiology, cell biology, biochemistry and immunology, which are well within the purview of the skilled artisan. Such techniques are explained fully in the literature, such as, "Molecular Cloning: A Laboratory Manual", second edition (Sambrook, 1989); "Oligonucleotide Synthesis" (Gait, 1984); "Animal Cell Culture" (Freshney, 1987); "Methods in Enzymology" "Handbook of Experimental Immunology" (Weir, 1996); "Gene Transfer Vectors for Mammalian Cells" (Miller and Calos, 1987); "Current Protocols in Molecular Biology" (Ausubel, 1987); "PCR: The Polymerase Chain Reaction", (Mullis, 1994); "Current Protocols in Immunology" (Coligan, 1991). These techniques are applicable to the production of the polynucleotides and polypeptides of the invention, and, as such, may be considered in making and practicing the invention. Particularly useful techniques for particular embodiments will be discussed in the sections that follow.

The following examples are put forth so as to provide those of ordinary skill in the art with a complete disclosure and description of how to make and use the assay, screening, and therapeutic methods of the invention, and are not intended to limit the scope of what the inventors regard as their invention.

EXAMPLES

Example 1: Transplantation of CX3CR1$^{+/GFP}$ Hematopoietic Cells Leads to Rapid Microglia Reconstitution Bone marrow cells were isolated from 8 weeks old CD45.2 wild type or CD45.2 CX3CR1$^{+/GFP}$ mice. After red blood lysis, 2.0×10$^6$ cells were intravenously (IV) transplanted into eight-week-old CD45.1 wild type busulfan conditioned recipients (25 mg/kg for four days). Transplanted mice were clinically monitored and sacrificed at 45, 90, and 180 days post-transplant (FIG. 1A). No inter-current deaths occurred. At sacrifice after perfusion, bone marrow and brain were collected to monitor the engraftment of the transplanted cells by flow cytometry. Brain cells were isolated after papain digestion and Percoll density gradient separation.

Figure 1B:
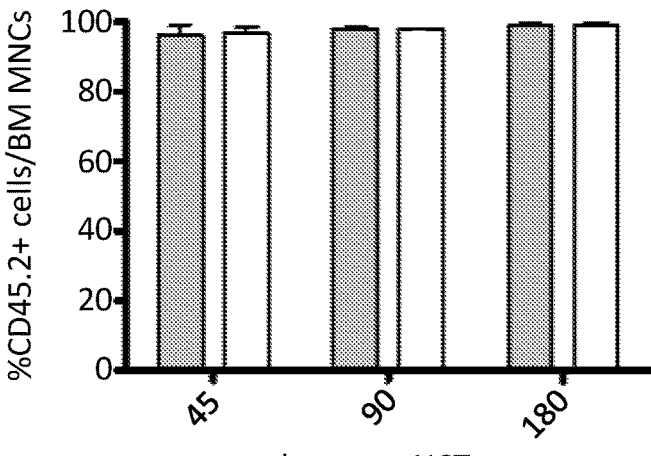
Figure 1C:
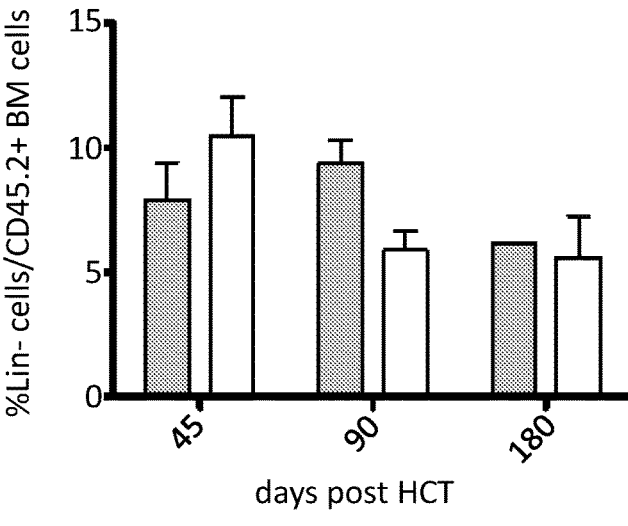
Figure 1D:
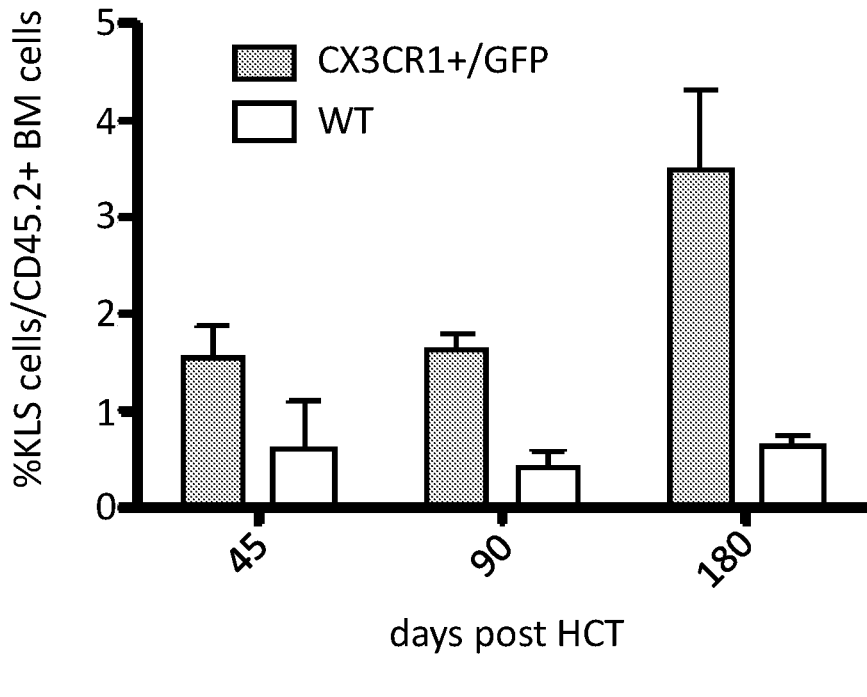
Figure 1E:
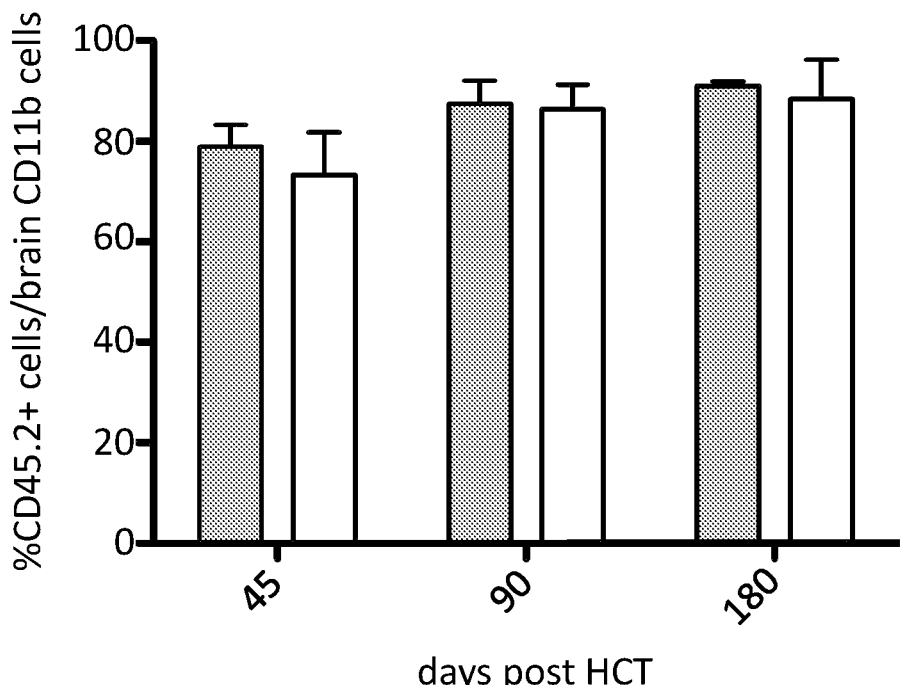
Figure 1F:
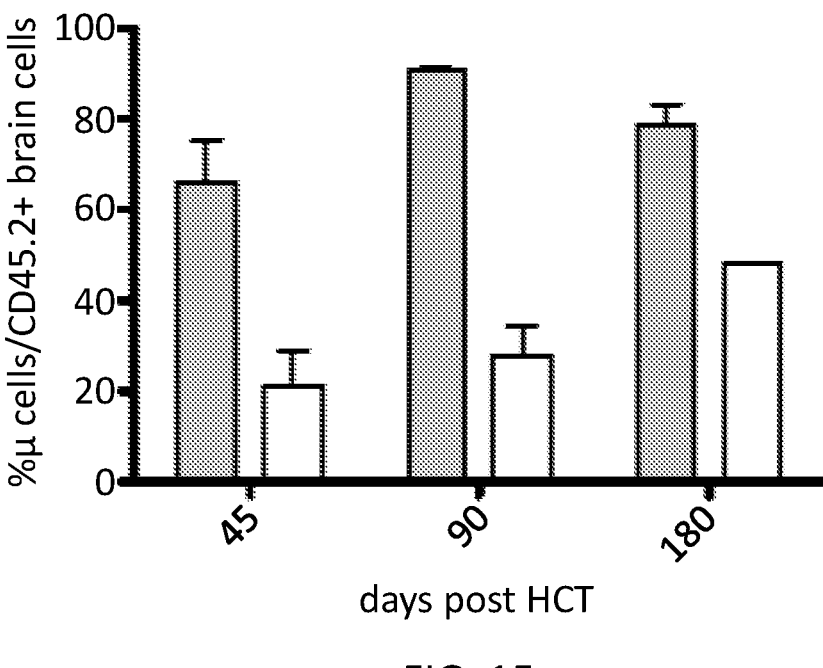
Figure 1G:
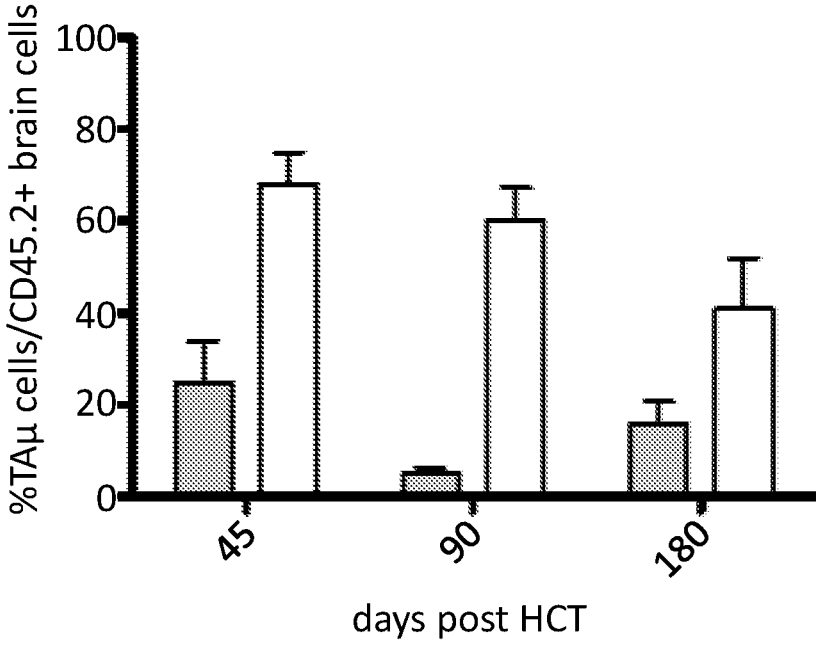
Figure 2A:
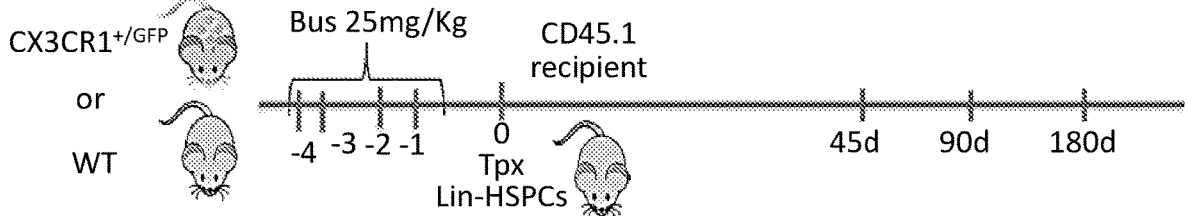
FIGS. 2A-2G compare engraftment of $CX3CR1^{+/GFP}$ and wild type $Lin^-$ HSPCs in recipients.
Figure 2B:
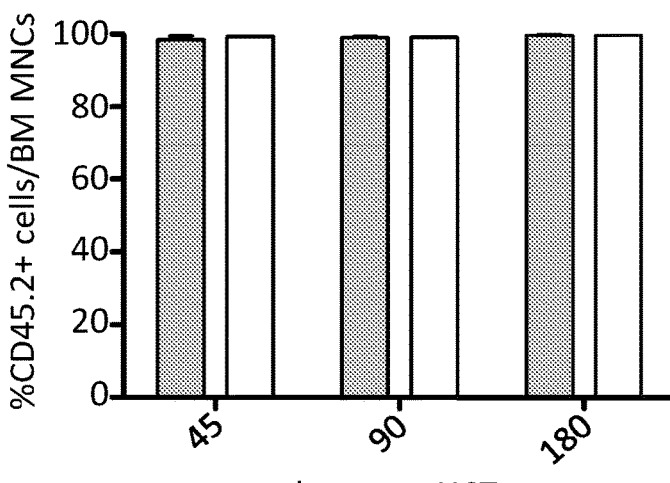
Figure 2C:
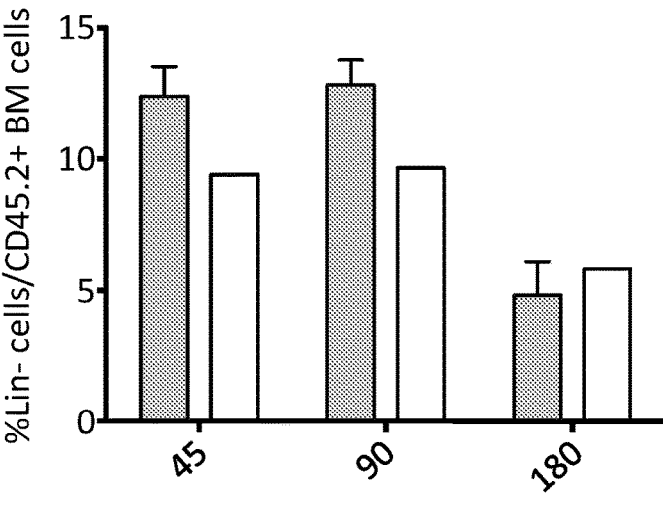
Figure 2D:
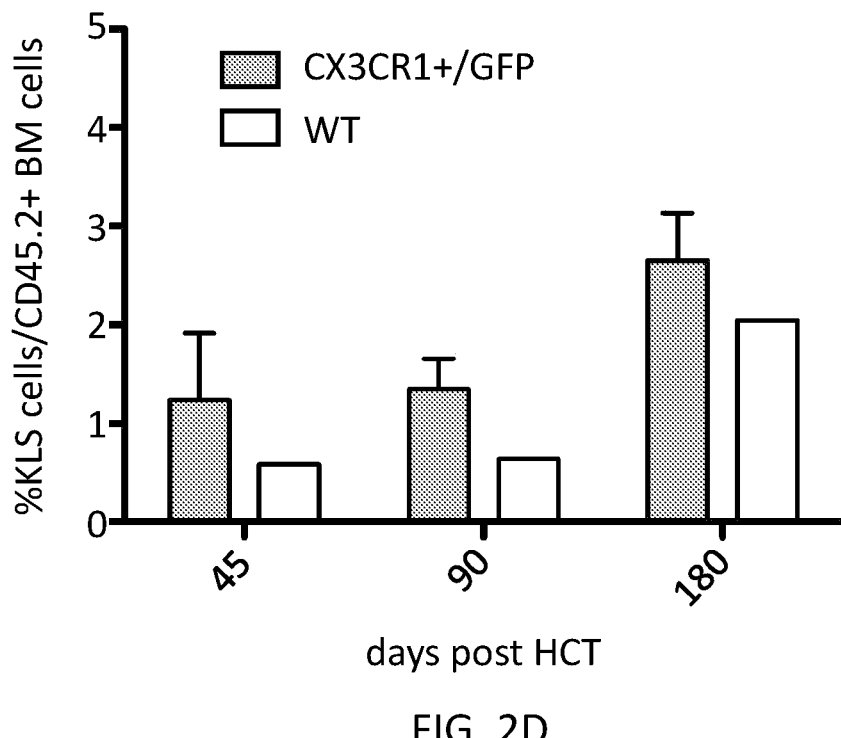
Figure 2E:
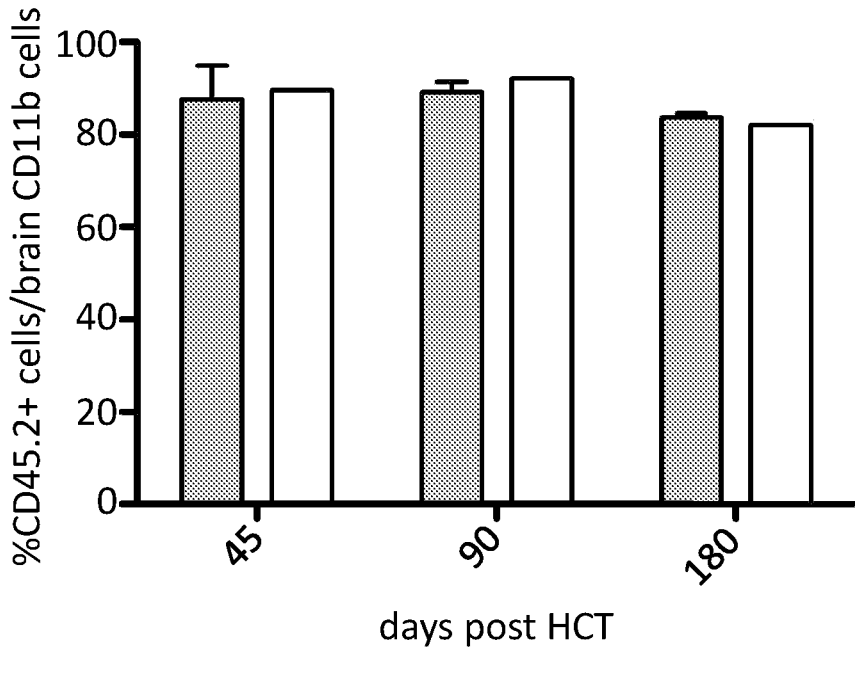
Figure 2F:
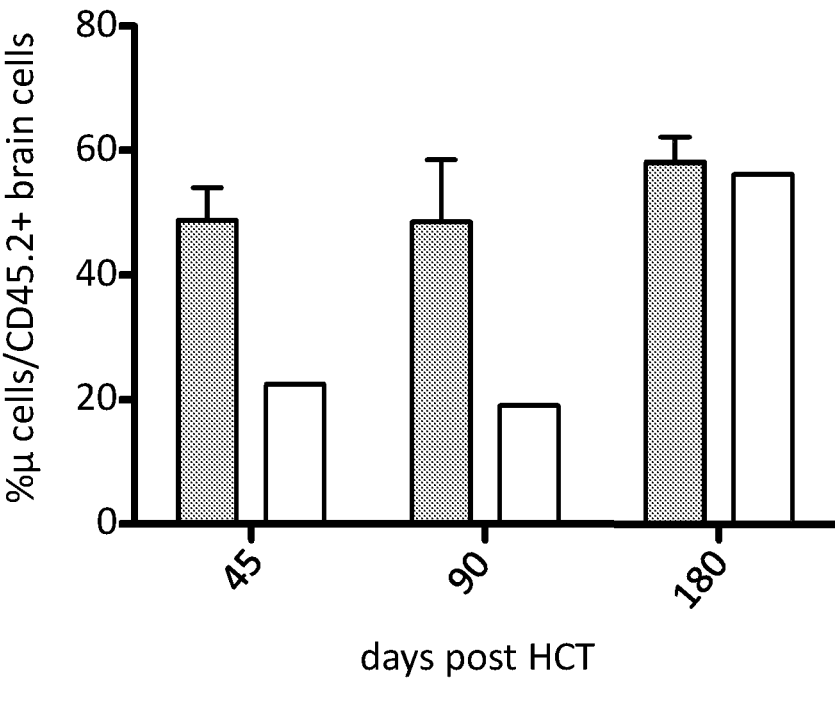
Figure 2G:
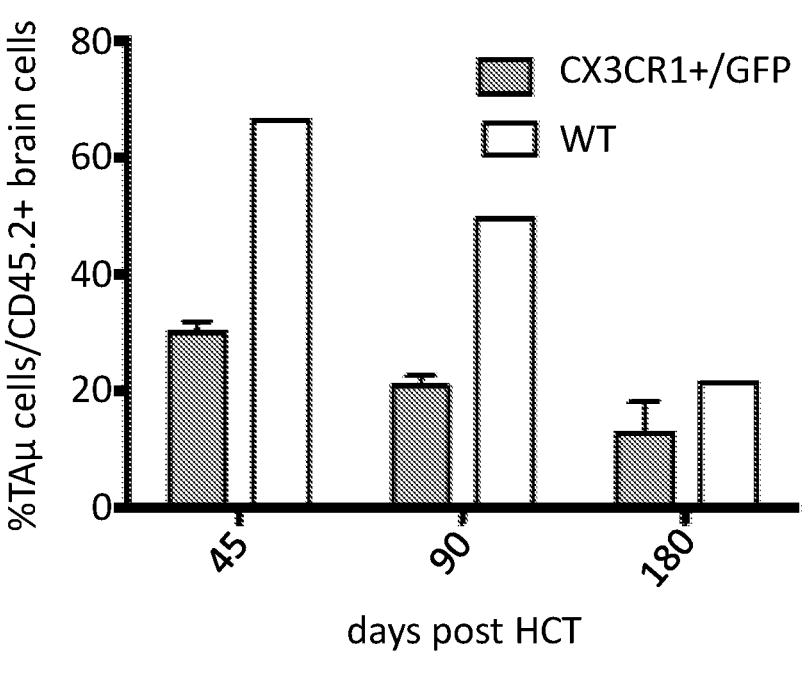

Similar sustained engraftments of the transplanted CX3CR1$^{+/GFP}$ and wild type cells was observed in the bone marrow of the recipients (FIG. 1B). A higher frequency of donor Kit$^+$ Lineage$^-$ Sca-1$^+$ (KLS) cells (a type of hematopoietic stem cells) was observed in mice receiving CX3CR1$^{+/GFP}$ versus wild type cells (FIGS. 1B-1D). In the brain, a similar overall CD45.2 donor cell engraftment was observed in CX3CR1$^{+/GFP}$ and wild type cell recipients (FIGS. 1E-1G). However, a different proportion of CD45$^+$ CD11$^+$ myeloid cell subpopulations was observed in mice receiving cells isolated from different donors. In particular, a faster appearance of the more mature microglia-like CD45$^{low}$ CD11b$^{high}$ cells versus the more immature transiently amplifying μ (TAμ) CD45$^{high}$ CD11b$^{low}$ cells was observed in mice transplanted with CX3CR1$^{+/GFP}$ versus wild type cells (FIGS. 1E-1G).

Similar results were obtained when CX3CR1$^{+/GFP}$ hematopoietic stem progenitor cells (Lin$^-$) were transplanted (1×10$^6$ Lin$^-$ cells/mouse, after busulfan conditioning) (FIGS. 2A-2G).

Figure 3A:
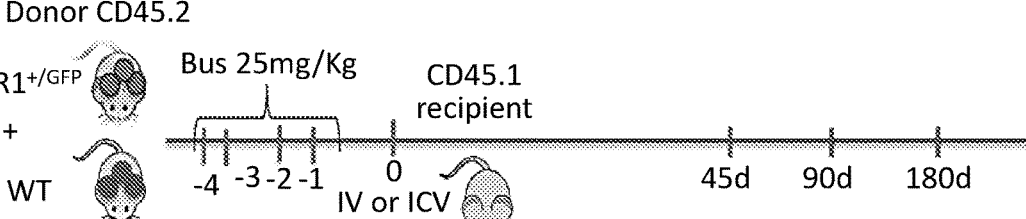
FIGS. 3A-3G demonstrate engraftment of $CX3CR1^{+/GFP}$ and wild type Lin$^-$ HSPCs in competitive transplant recipients.
Figure 3B:
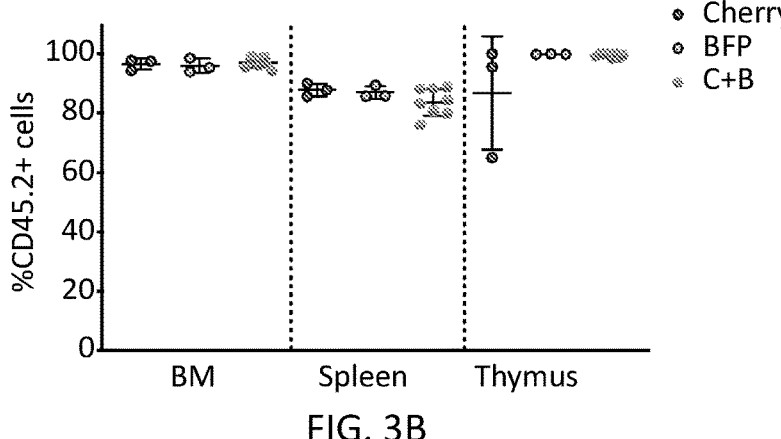
Figure 3C:
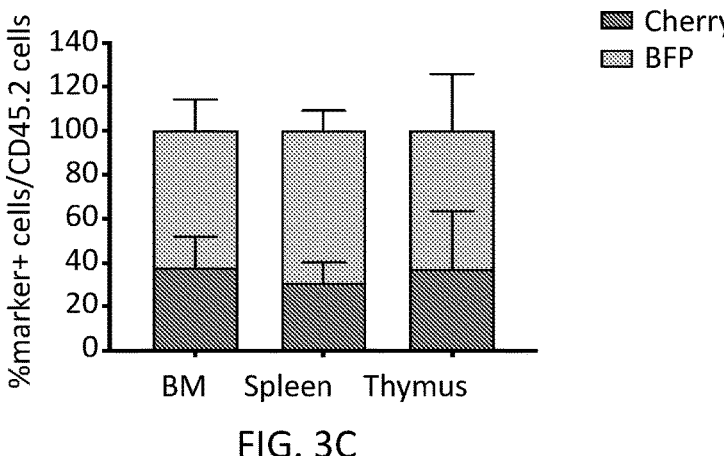

Example 2: CX3CR1$^{+/GFP}$ Hematopoietic Stem Progenitor Cells (HSPCs) have a Competitive Advantage Upon Transplantation To better characterize the phenotype of CX3CR1$^{+/GFP}$ cells and assess whether they could have a qualitative (and quantitative) advantage over wild type cells, competitive transplant experiments were performed. HSPCs were isolated from eight-week-old CD45.2 wild type or CD45.2 CX3CR1$^{+/GFP}$ mice, labeled with lentiviral vectors (LV) encoding for different fluorescent markers (PGK.mCherry and PGK.blue fluorescent protein (BFP), respectively), and co-transplanted at 1:1 ratio in CD45.1 busulfan myeloablated recipients (FIG. 3A).

Transplantation was performed employing intravenous (IV) and intracerebroventricular (ICV) administration in independent experiments. In the IV setting, a total of 1.0× 10$^6$ HSPCs were transplanted per mouse. In the ICV setting, a total of 0.3×10$^6$ HSPCs were transplanted per mouse. Mice receiving HSPCs via ICV administration were also provided with 2.0×10$^6$ total bone marrow untransduced CD45.1 cells intravenously, for recovery from aplasia five days after transplant. Transplantations of single populations of mCherry$^+$ wild type HSPCs or BFP+CX3CR1$^{+/GFP}$ HSPCs were also performed as control.

Figure 3D:
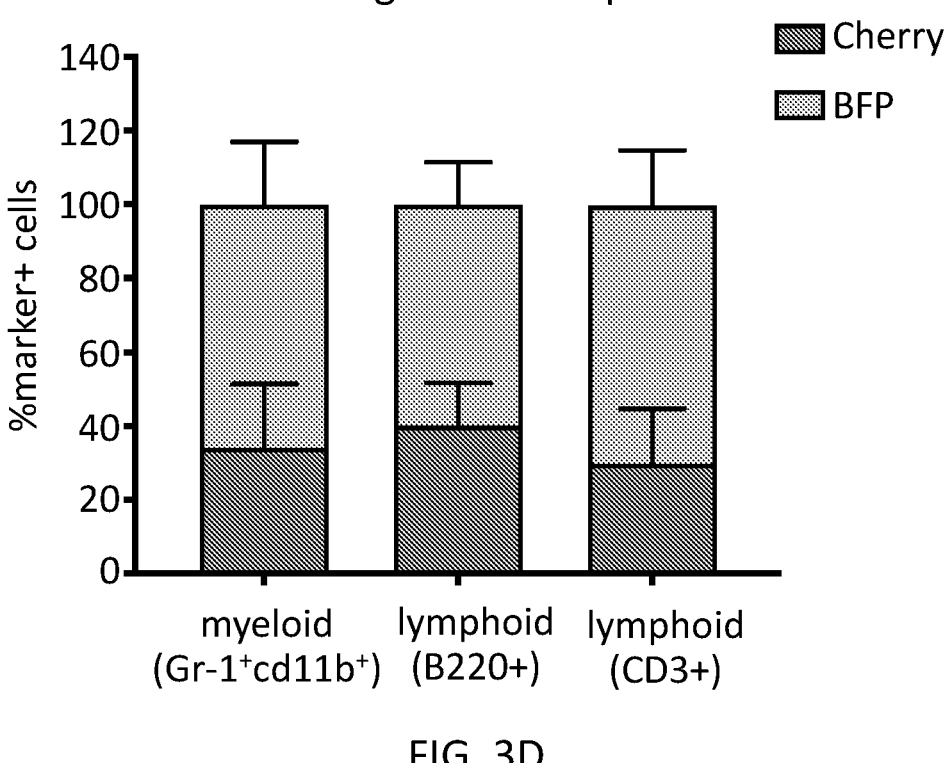
Figure 3E:
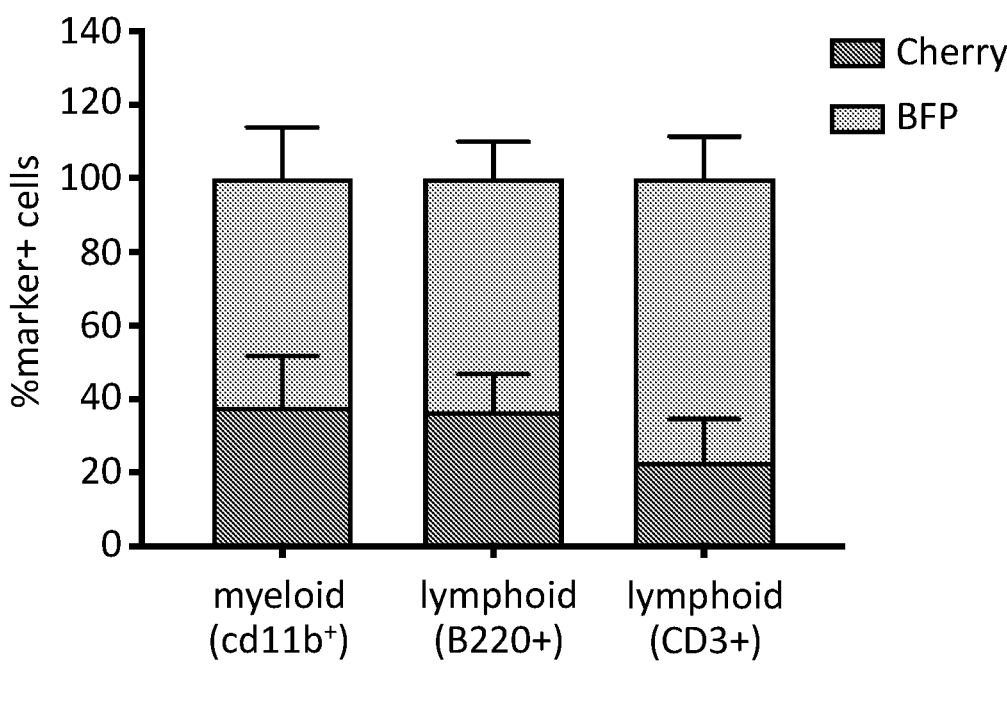

Good engraftment of donor cells (CD45.2) was observed in all the groups at bleeding performed one-month post-transplant. All the mice were sacrificed at 45 days post-transplant, showing good engraftment of donor cells (CD45.2) in all analyzed tissues and groups (FIGS. 3B-3G). CX3CR1$^{+/GFP}$ HSPCs showed a consistent and robust quantitative advantage in engraftment over wild type in the competitive setting in all analyzed tissues (bone marrow, spleen, and brain) (FIGS. 3C-3G). The advantage of haplo-insufficient versus wild type cells was observed both in lymphoid and myeloid lineages in all analyzed hematopoietic tissues (FIGS. 3D-3E). Notably, animals transplanted with CX3CR1$^{+/GFP}$ or wild type HSPCs, or a combination of the two showed a similar representation of myeloid and lymphoid populations in all the tissues analyzed. Very little to no donor cell engraftment was detected in hematopoietic organs of ICV transplanted animals.

Figure 3F:
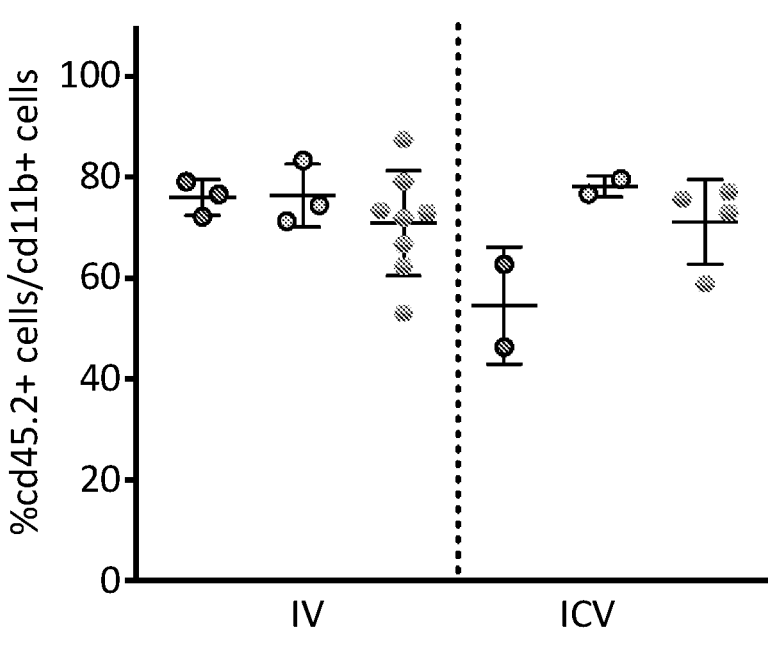
Figure 3G:
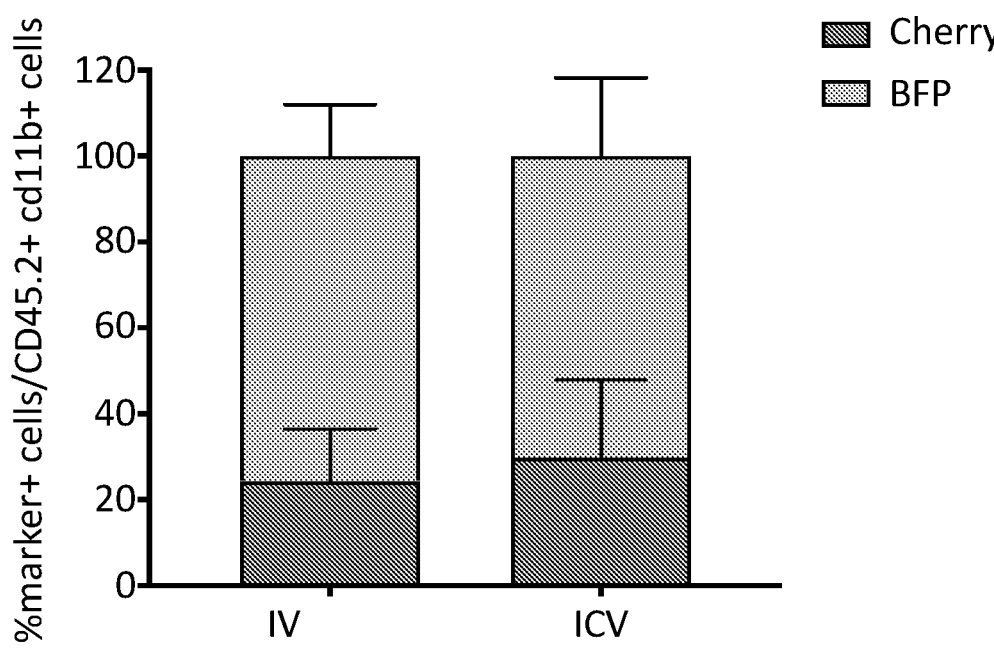

A good engraftment of donor cells was observed in the brain of both IV and ICV transplanted animals (FIG. 3F). Also, in the brain of the competitively transplanted animals, CX3CR1$^{+/GFP}$ cells were more represented than wild type cells within the CD11b$^+$ hematopoietic donor cell fraction (FIG. 3G).

Overall these data suggested that HSPCs haplo-insufficient at the CX3CR1 locus have a greater ability to engraft and/or generate a mature progeny as compared to normal cells when co-transplanted in myeloablated host. This was also true for central nervous system engrafted haplo-insufficient cells.

Example 3: CX3CR1$^{+/GFP}$ HSPCs Generate More Mature Microglia-Like Cells than Wild Type HSPCs Upon Transplantation In order to confirm that CX3CR1 haplo-insufficiency could be also associated with more rapid maturation of transplanted cells and/or their progeny, particularly in the brain, cells engrafted in the brain of competitively transplanted mice were analyzed for their morphology and for the expression of microglia associated genes.

Figures 4A, 4B:
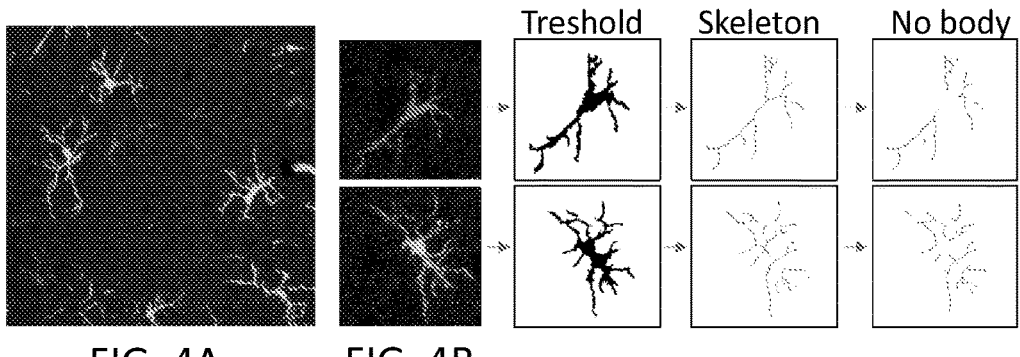
Figure 4C:
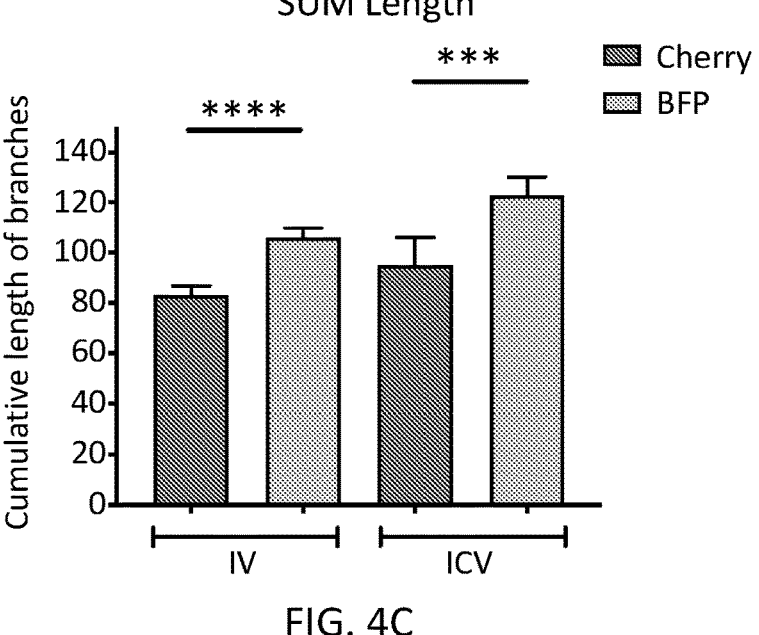
Figure 4D:
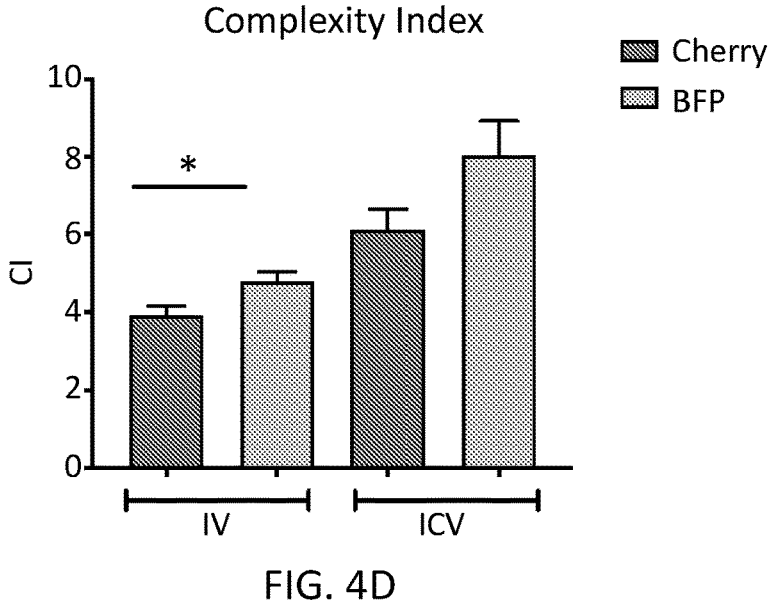
Figure 4E:
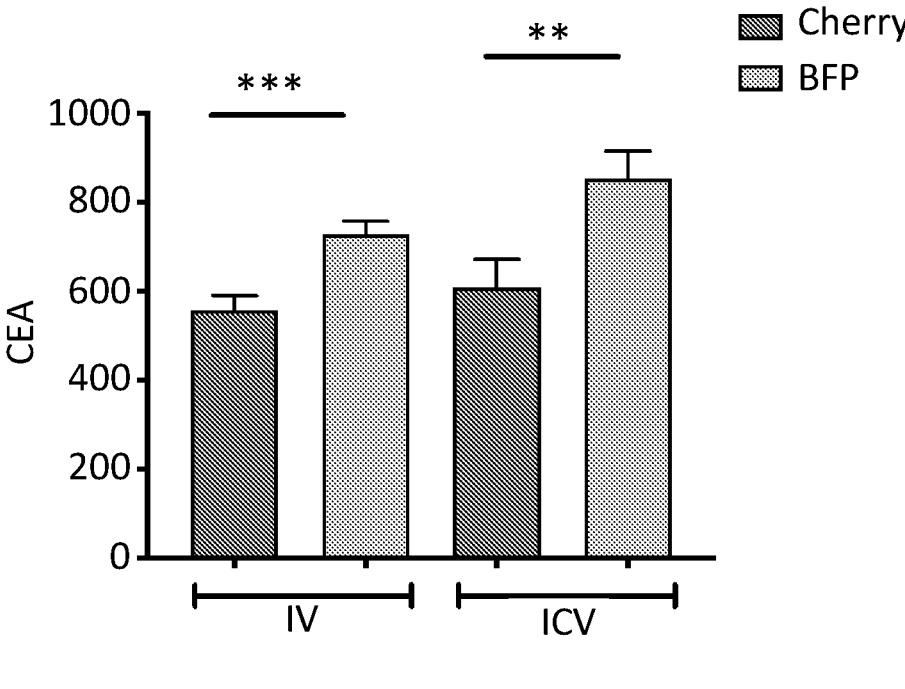

Different parameters reported in literature to be valuable criteria in describing microglia morphology (Verdonk et al. 2016) were assessed. These parameters included the total length of ramifications (Sum Length); the Complexity Index (CI), defined as the ratio of the number of segments of each cell and the number of its primary ramifications, wherein a segment is the length of process between two nodes; the covered environment area (COA) that defines the 2D total surface covered by cell ramifications and described as the area of the polygon formed by linking the extremities of its processes, expressed in μm$^2$. CX3CR1$^{+/GFP}$ cells and wild type cells on brain tissues slices from the cortex of competitive transplant recipient mice sacrificed 45 days post-transplant were analyzed. The analysis was carried out manually, using a macro running on the Fiji program, designed to render the process unbiased (FIGS. 4A, 4B). In both the IV and ICV settings, CX3CR1$^{+/GFP}$ BFP cells had longer ramifications and a greater complexity of their ramifications, and cover a larger area as compared to Cherry wild type cells (FIGS. 4C-4E). To exclude any possible bias due to the different signal/expression of the two reporter genes, the same analysis was performed based on allograft inflammatory factor 1 (Iba-1) expression in both wild type and $CX3CR1^{+/GFP}$ cells. No differences were observed in all the parameters analyzed, indicating that fluorescent markers can be used for rapid evaluation of these parameters. Overall, these data suggest that $CX3CR1^{+/GFP}$ cells have a more mature morphology than wild type cells.

Figure 4F:
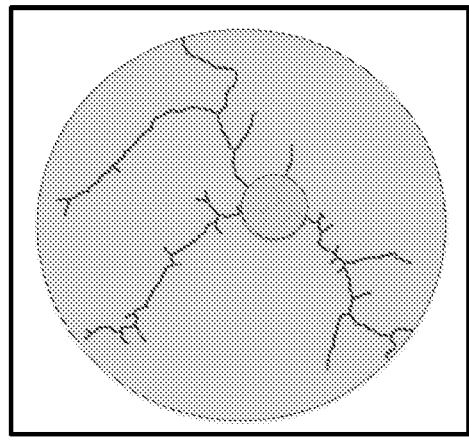
Figure 4G:
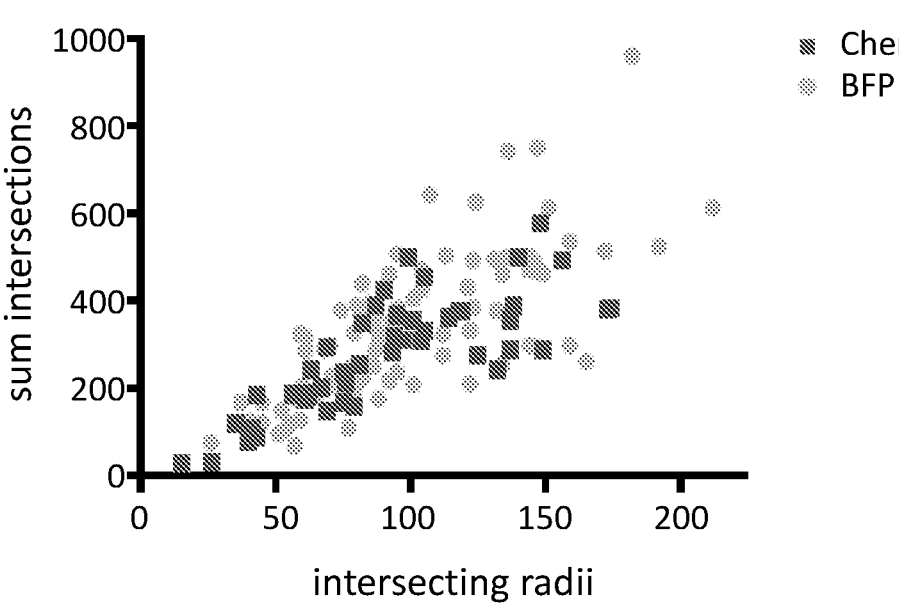
Figure 4H:
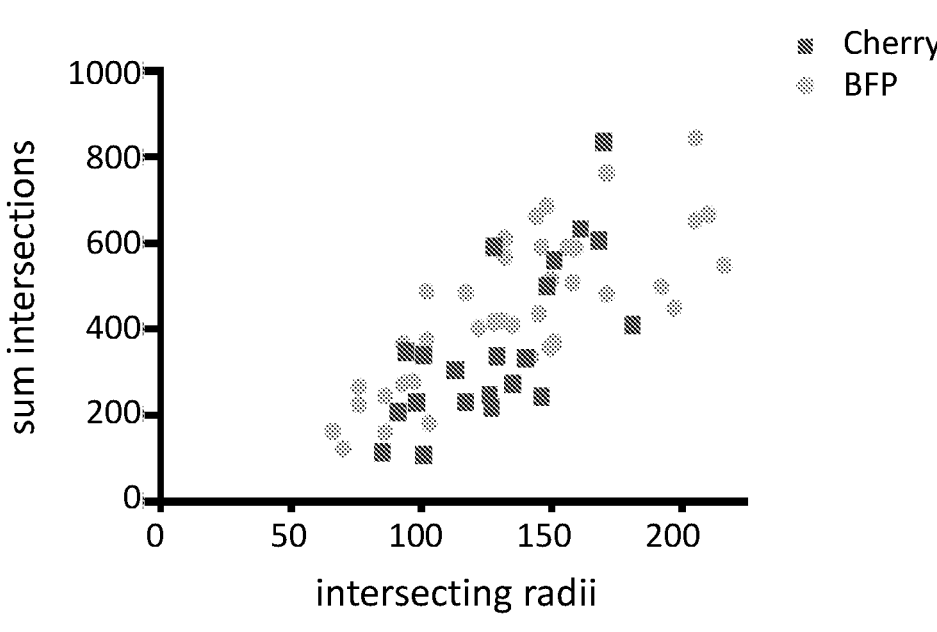

To validate the results, a Sholl Analysis was performed by counting the number of intersections for concentric circles, centered at the centroid of the cell body, of gradually increasing radiuses (FIG. 4F). By plotting the sum of intersection and the intersecting radii it is possible to visualize the distribution of cells, according to their complexity. In both the IV and ICV settings, $CX3CR1^{+/GFP}$ cells were more spread and distributed in the (upper) right quadrants of the graph, indicating a more mature phenotype as compared to wild type cells (FIGS. 4G, 4H).

Figure 5:
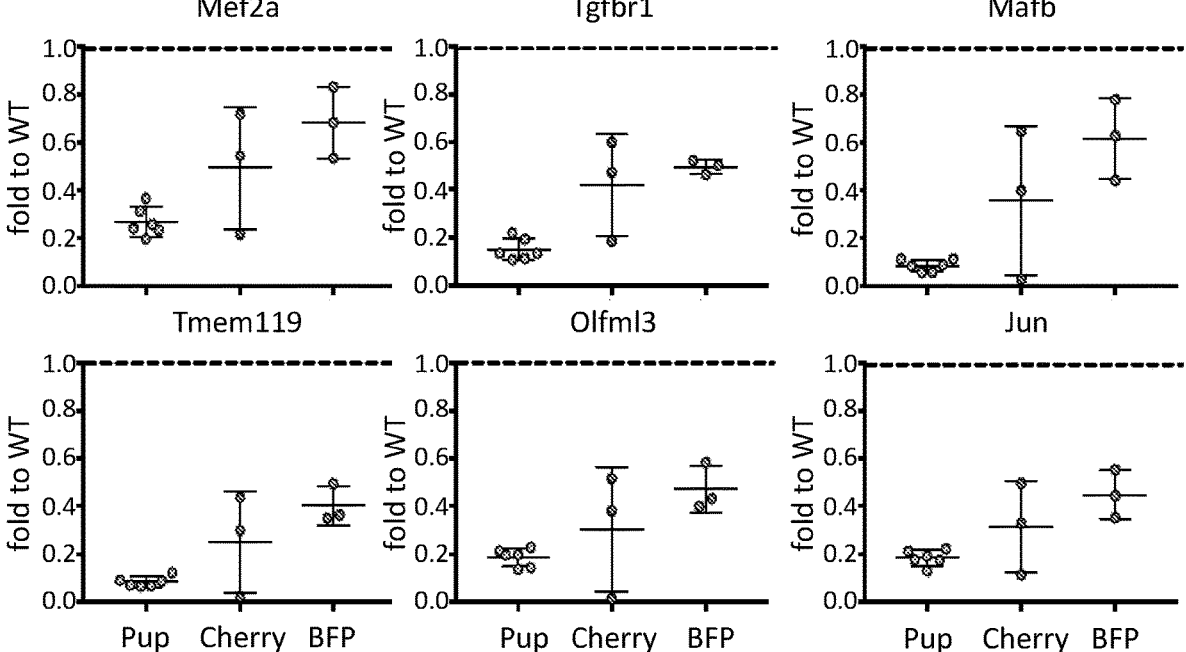
FIG. 5 is a series of graphs showing the mRNA expression of microglia-associated genes by the marker-positive sorted progeny of the IV transplanted $CX3CR1^{+/GFP}$ or WT cells in competitive transplant recipients. Expression of each gene in FACS-sorted CD11b$^+$ CD45$^+$ marker-positive (BFP versus Cherry) brain cells and in CD11b$^+$ CD45$^+$ brain cells isolated from neonate post-natal day 3 animals (pup) is shown in comparison to the expression of the same genes in adult WT not transplanted reference mice.

To determine whether wild type and CX3CR1 haploinsufficient microglia-like cells in the brain of transplanted animals express genes differently during maturation, microglia signature genes as well as transcription factors associated with microglia maturation (Butovsky et al., 2014) were assessed in microglia-like cells. These cells were sorted according to the expression of BFP (haploinsufficient cells) and Cherry (wild type cells) from the brain of competitively transplanted mice at the time of sacrifice. RNA was extracted from sorted cells and cDNA was generated and amplified using SuperScript VILO Master mix and Custom TaqMan PreAmp Pools (Thermo Fisher Scientific). Gene expression analysis was performed using a custom designed TaqMan-based microfluidic card gene expression assay (Applied Biosystems). Pups (post-natal day 3 neonates) and age-matched untreated wild type microglia cells were used as references for the analysis. Unexpectedly, for some of the analyzed genes higher expression levels, similar to those observed in adult microglia isolated from untreated wild type mice, were observed in CX3CR1 haploinsufficient cells as compared to wild type cells (FIG. 5). These results may support the conclusion reported above about a more rapid maturation of CX3CR1 haplo-insufficient cells.

Example 4: $CX3CR1^{GFP/GFP}$ HSPCs have a Quantitative Repopulation Advantage, as Haplo-Insufficient $CX3CR1^{+/GFP}$ HSPCs, Over WT HSPCs To better understand the functional role of the CX3CR1 axis in post-transplant repopulation, competitive transplant experiments were performed with CX3CR1 homozygous defective cells similarly to those performed employing haploinsufficient HSPCs. The IV route of cell delivery was adopted for the transplant, which resulted in more striking results of haplo-insufficient HSPCs advantage in the brain and contributed to hematopoietic organ reconstitution.

Figure 6A:
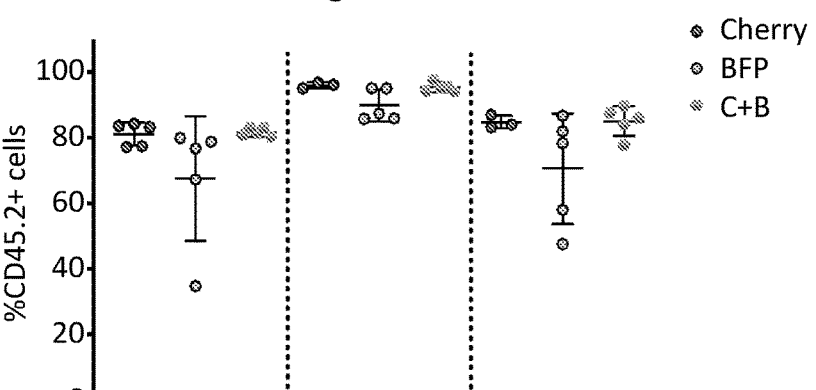
FIGS. 6A-6F demonstrate engraftment of $CX3CR1^{GFP/GFP}$ and wild type Lin$^-$ HSPCs in competitive transplant recipients.

HSPCs were isolated from eight-week-old CD45.2 wild type or CD45.2 $CX3CR1^{GFP/GFP}$ mice labeled with lentiviral vectors (LV) encoding for different fluorescent markers (PGK.mCherry and PGK.blue fluorescent protein (BFP), respectively), and co-transplanted at a 1:1 ratio in CD45.1 busulfan myeloablated recipients in independent experiments (FIG. 6A). A total of $1.0 \times 10^6$ HSPCs were transplanted per mouse ($0.5*10^6$ mCherry$^+$HSPCs+$0.5*10^6$ BFP$^+$ $CX3CR1^{GFP/GFP}$ HSPCs in the competitive transplanted animals). Transplantations of single populations of mCherry$^+$ wild type HSPCs or BFP+$CX3CR1^{GFP/GFP}$ HSPCs were also performed as control.

Figure 6B:
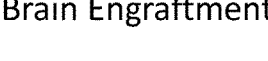

After transplant, mice were monitored and sacrificed at the same short-term time point assessed in the haploinsufficient setting (45 days). Peripheral blood (PB) was collected by bleeding the mice at 30 days post-transplant and hematopoietic organs (BM, spleen) and brain were collected after perfusion at sacrifice. Overall, engraftment of the donor cells (% CD45.2) in hematopoietic organs was similar between wild type and $CX3CR1^{GFP/GFP}$ cells, although a slightly reduced engraftment of $CX3CR1^{GFP/GFP}$ cells was observed in PB, BM and spleen (FIG. 6B). Relative proportions within the donor cell population showed a quantitative advantage of $CX3CR1^{GFP/GFP}$ over wild type cells in all hematopoietic tissues (FIG. 6D). The advantage observed was less striking than when haplo-insufficient $CX3CR1^{+/GFP}$ cells were transplanted in competition with wild type cells in the same experimental setting. Of note, control mice transplanted with wild type only or $CX3CR1^{GFP/GFP}$ only HSPCs showed high frequency of the transduced cells (mCherry+: 99,43+/−0,2; BFP+: 99,2+/−0, 44), confirming the reliability of the analysis based on LV reporter gene-expression. The advantage of $CX3CR1^{GFP/GFP}$ versus wild type cells was observed both in lymphoid and myeloid lineages in all the analyzed hematopoietic tissues (FIGS. 6E, 6F). Notably, animals transplanted with $CX3CR1^{GFP/GFP}$ or wild type HSPCs, or with a combination of the two, showed a similar representation of myeloid and lymphoid populations in all the tissues analyzed.

Figure 6C:
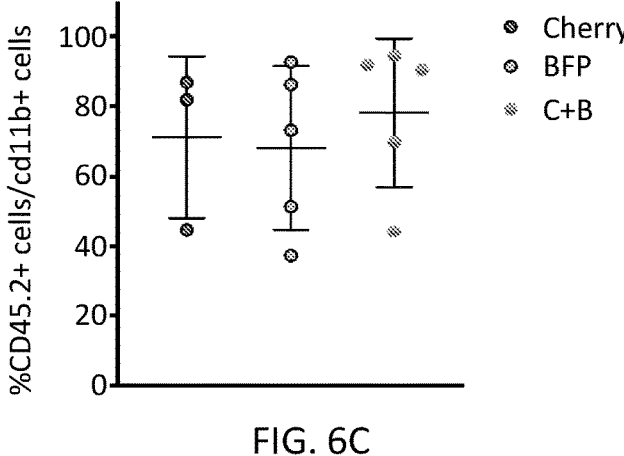
Figure 6D:
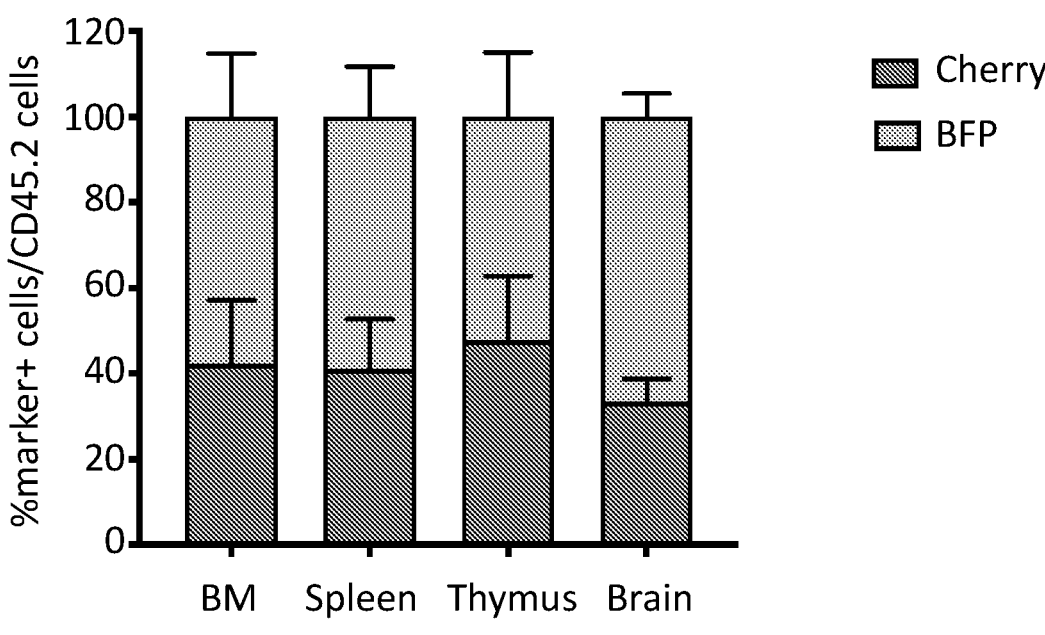
Figure 6E:
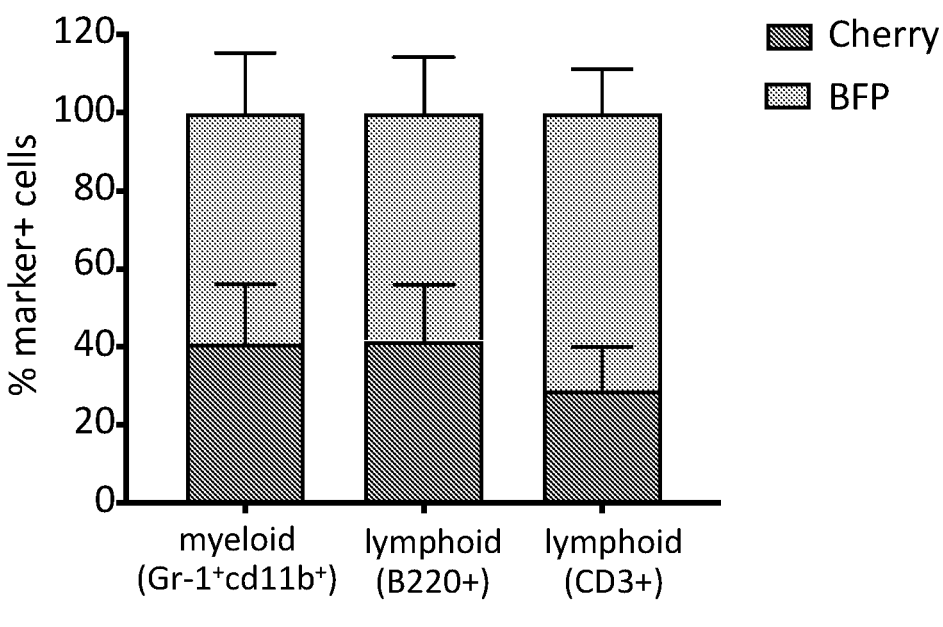
Figure 6F:
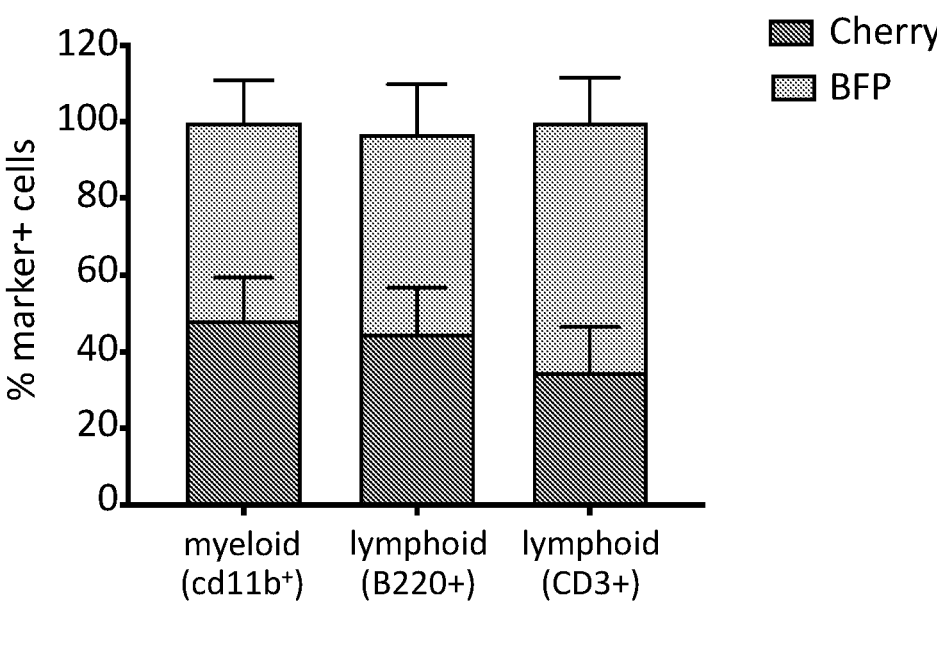

A good engraftment of donor cells was observed in the brain, with some variability observed within all experimental groups (FIG. 6C). In the brain of the competitively transplanted animals, $CX3CR1^{GFP/GFP}$ cells were more represented than wild type cells within the CD11b$^+$ hematopoietic donor cell fraction (FIG. 6D). This competitive advantage in the brain was more remarkable than that observed in hematopoietic organs.

These data confirm that a reduction of CX3CR1 expression in HSPCs resulted in an engraftment advantage in hematopoietic organs and was more pronounced in brain-associated myeloid populations. These data also support a role of the CX3CR1 axis in the mechanism of myeloid cell reconstitution following HSPC transplantation.

Example 5: Editing at the CX3CR1 Locus in Human HSPCs

A targeted gene addition approach is being designed to insert at least one gene at the CX3CR1 locus in human HSPCs and their progeny that will be expressed in their microglia-like progeny upon engraftment. Haploinsufficiency at this locus upon targeted therapeutic gene addition may also confer to the edited HSPCs a repopulation and maturation advantage over wild type cells.

Different guides are being tested for specificity of targeting and reducing CX3CR1 expression in CD34$^+$ human HSPCs. The population of CD34$^+$ cells to be infused is being characterized by Tracking of Indels by DEcomposition (TIDE) analysis for evaluating the distribution of haploinsufficient, knockout, and wild type cells. Edited cells are being characterized for the expression of CX3CR1 by flow cytometry and for their ability to engraft into the CNS of immune-deficient mouse recipients.

Other Embodiments

From the foregoing description, it will be apparent that variations and modifications may be made to the invention described herein to adopt it to various usages and conditions. Such embodiments are also within the scope of the following claims.

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

All patents and publications mentioned in this specification are herein incorporated by reference to the same extent as if each independent patent and publication was specifically and individually indicated to be incorporated by reference.

What is claimed is:

1. A CX3CR1 haploinsufficent cell comprising an exogenous nucleic acid molecule inserted into one allele of a CX3CR1 gene, wherein the insertion disables the one allele of the CX3CR1 gene.

2. The CX3CR1 haploinsufficent cell of claim 1, wherein the exogenous nucleic acid molecule encodes a therapeutic polynucleotide or polypeptide.

3. The CX3CR1 haploinsufficient cell of claim 2, wherein the therapeutic polynucleotide or polypeptide is neuroprotective.

4. A pharmaceutical composition comprising the CX3CR1 haploinsufficient cell of claim 1.

5. A kit comprising the CX3CR1 haploinsufficient cell of claim 1, and directions for the administration of the cell to a subject in need thereof.

6. A kit comprising the pharmaceutical composition of claim 4.

7. A method of reconstituting microglia cells in a subject, the method comprising administering to the subject the CX3CR1 haploinsufficient cell of claim 1.

8. A method of reconstituting microglia cells in a subject, the method comprising administering to the subject the pharmaceutical composition of claim 4.

9. A method of treating a metabolic or neurological disease in a subject, the method comprising administering to the subject the CX3CR1 haploinsufficient cell of claim 1.

10. The method of claim 7, wherein the administering is intracerebroventricular.

11. The method of claim 7, wherein the administering is intravenous.

12. The method of claim 7, further comprising ablative conditioning prior to administering the CX3CR1 haploinsufficient cell.

13. The method of claim 12, wherein ablative conditioning comprises administering an alkylating agent capable of ablating endogenous microglia cells.

14. The method of claim 13, wherein the alkylating agent is busulfan.

* * * * *

SEQUENCE LISTING

```
<160> NUMBER OF SEQ ID NOS: 2

<210> SEQ ID NO 1
<211> LENGTH: 355
<212> TYPE: PRT
<213> ORGANISM: Homo sapiens

<400> SEQUENCE: 1

Met Asp Gln Phe Pro Glu Ser Val Thr Glu Asn Phe Glu Tyr Asp Asp
1               5                   10                  15

Leu Ala Glu Ala Cys Tyr Ile Gly Asp Ile Val Val Phe Gly Thr Val
            20                  25                  30

Phe Leu Ser Ile Phe Tyr Ser Val Ile Phe Ala Ile Gly Leu Val Gly
        35                  40                  45

Asn Leu Leu Val Val Phe Ala Leu Thr Asn Ser Lys Lys Pro Lys Ser
    50                  55                  60

Val Thr Asp Ile Tyr Leu Leu Asn Leu Ala Leu Ser Asp Leu Leu Phe
65                  70                  75                  80

Val Ala Thr Leu Pro Phe Trp Thr His Tyr Leu Ile Asn Glu Lys Gly
                85                  90                  95

Leu His Asn Ala Met Cys Lys Phe Thr Thr Ala Phe Phe Phe Ile Gly
            100                 105                 110

Phe Phe Gly Ser Ile Phe Phe Ile Thr Val Ile Ser Ile Asp Arg Tyr
            115                 120                 125

Leu Ala Ile Val Leu Ala Ala Asn Ser Met Asn Asn Arg Thr Val Gln
    130                 135                 140

His Gly Val Thr Ile Ser Leu Gly Val Trp Ala Ala Ala Ile Leu Val
145                 150                 155                 160

Ala Ala Pro Gln Phe Met Phe Thr Lys Gln Lys Glu Asn Glu Cys Leu
                165                 170                 175

Gly Asp Tyr Pro Glu Val Leu Gln Glu Ile Trp Pro Val Leu Arg Asn
            180                 185                 190

Val Glu Thr Asn Phe Leu Gly Phe Leu Leu Pro Leu Leu Ile Met Ser
            195                 200                 205

Tyr Cys Tyr Phe Arg Ile Ile Gln Thr Leu Phe Ser Cys Lys Asn His
    210                 215                 220

Lys Lys Ala Lys Ala Ile Lys Leu Ile Leu Leu Val Val Ile Val Phe
225                 230                 235                 240

Phe Leu Phe Trp Thr Pro Tyr Asn Val Met Ile Phe Leu Glu Thr Leu
                245                 250                 255

Lys Leu Tyr Asp Phe Phe Pro Ser Cys Asp Met Arg Lys Asp Leu Arg
            260                 265                 270

Leu Ala Leu Ser Val Thr Glu Thr Val Ala Phe Ser His Cys Cys Leu
        275                 280                 285

Asn Pro Leu Ile Tyr Ala Phe Ala Gly Glu Lys Phe Arg Arg Tyr Leu
    290                 295                 300

Tyr His Leu Tyr Gly Lys Cys Leu Ala Val Leu Cys Gly Arg Ser Val
305                 310                 315                 320

His Val Asp Phe Ser Ser Ser Glu Ser Gln Arg Ser Arg His Gly Ser
```

-continued

```
                325                    330                    335
Val Leu Ser Ser Asn Phe Thr Tyr His Thr Ser Asp Gly Asp Ala Leu
            340                    345                    350

Leu Leu Leu
        355

<210> SEQ ID NO 2
<211> LENGTH: 1487
<212> TYPE: DNA
<213> ORGANISM: Homo sapiens

<400> SEQUENCE: 2
ggggcagatc cagattccct ttgcagtcca cgccaggcct tcaccatgga tcagttccct       60
gaatcagtga cagaaaactt tgagtacgat gatttggctg aggcctgtta tattgggggac      120 atcgtggtct ttgggactgt gttcctgtcc atattctact ccgtcatctt tgccattggc      180
ctggtgggaa atttgttggt agtgtttgcc ctcaccaaca gcaagaagcc caagagtgtc      240
accgacattt acctcctgaa cctggccttg tctgatctgc tgtttgtagc cactttgccc      300
ttctggactc actatttgat aaatgaaaag ggcctccaca atgccatgtg caaattcact      360
accgccttct tcttcatcgg cttttttgga agcatattct tcatcaccgt catcagcatt      420
gataggtacc tggccatcgt cctggccgcc aactccatga acaaccggac cgtgcagcat      480
ggcgtcacca tcagcctagg cgtctgggca gcagccattt tggtggcagc accccagttc      540
atgttcacaa agcagaaaga aaatgaatgc cttggtgact accccgaggt ccttcaggaa      600
atctggcccg tgctccgcaa tgtggaaaca aattttcttg gcttcctact ccccctgctc      660
attatgagtt attgctactt cagaatcatc cagacgctgt tttcctgcaa gaaccacaag      720
aaagccaaag ccattaaact gatccttctg gtggtcatcg tgtttttcct cttctggaca      780
ccctacaacg ttatgatttt cctggagacg cttaagctct atgacttctt tcccagttgt      840
gacatgagga aggatctgag gctggccctc agtgtgactg agacggttgc atttagccat      900
tgttgcctga atcctctcat ctatgcattt gctggggaga agttcagaag ataccttac      960 cacctgtatg ggaaatgcct ggctgtcctg tgtgggcgct cagtccacgt tgatttctcc     1020
tcatctgaat cacaaaggag caggcatgga agtgttctga gcagcaattt tacttaccac     1080
acgagtgatg gagatgcatt gctccttctc tgaagggaat cccaaagcct tgtgtctaca     1140
gagaacctgg agttcctgaa cctgatgctg actagtgagg aagatttttg ttgttatttc     1200
ttacaggcac aaaatgatgg acccaatgca cacaaaacaa ccctagagtg ttgttgagaa     1260
ttgtgctcaa aatttgaaga atgaacaaat tgaactcttt gaatgacaaa gagtagacat     1320
ttctcttact gcaaatgtca tcagaacttt ttggtttgca gatgacaaaa attcaactca     1380
gactagttta gttaaatgag ggtggtgaat attgttcata ttgtggcaca agcaaaaagg     1440
gtgtctgagc cctcaaagtg aggggaacca gggcctgagc caagcta                   1487
```